United States Patent [19]

Bambury et al.

[11] Patent Number: 5,070,215

[45] Date of Patent: Dec. 3, 1991

[54] VINYL CARBONATE AND VINYL CARBAMATE CONTACT LENS MATERIAL MONOMERS

[75] Inventors: Ronald E. Bambury, Fairport; David E. Seelye, Rochester, both of N.Y.

[73] Assignee: Bausch & Lomb Incorporated, Rochester, N.Y.

[21] Appl. No.: 346,204

[22] Filed: May 2, 1989

[51] Int. Cl.$^5$ .............................. C07F 7/08; C07F 7/10
[52] U.S. Cl. ..................... 556/418; 556/420; 556/429; 556/437; 556/440; 544/229
[58] Field of Search ............... 556/420, 418, 429, 437, 556/440; 544/229

[56] References Cited

U.S. PATENT DOCUMENTS

| | | | |
|---|---|---|---|
| 4,153,641 | 6/1986 | Deichert et al. | 260/827 |
| 4,189,546 | 7/1986 | Deichert et al. | 528/26 |
| 4,195,030 | 7/1986 | Deichert et al. | 260/448.2 |
| 4,837,349 | 6/1989 | Ohfune et al. | 556/420 |
| 4,861,908 | 8/1989 | Satoh et al. | 556/420 |

FOREIGN PATENT DOCUMENTS 0079814  5/1983  European Pat. Off. .

OTHER PUBLICATIONS

Vol. 24, Journal of Polymer Science, Part C, pp. 75–88 (1968) "Poly(vinyl Chloroformate) & Derivatives: Preparation & Properties", J. R. Schaefgen.
Vol. 4, Polymer Bulletin 4, pp. 705–710 (1981), Gilles Meunier et al., "Polymerization & Copolymerization of Vinyl Carbamates & Vinyl Carbonates".
Vol. 16, Polymer Bulletin 16, pp. 391–394 (1986), Bernard Boutevin et al., "Polymerization—Synthesis & Polymerization of Fluorinated, Chlorinated & Deuterated Vinyl Carbonates".

*Primary Examiner*—Paul F. Shaver
*Attorney, Agent, or Firm*—Craig E. Larson; Christopher E. Blank; Salvatore P. Pace

[57] ABSTRACT

Novel monomers of the general formula

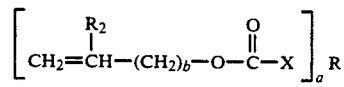

where b is 0 or 1, a is 1, 2, 3 or 4, $R^2$ is a monovalent alkyl radical and R is an organic radical. The novel monomers may be employed to produce novel copolymers useful as hydrogel, soft non-hydrogel and/or rigid gas permeable contact lens materials.

8 Claims, No Drawings

VINYL CARBONATE AND VINYL CARBAMATE CONTACT LENS MATERIAL MONOMERS

BACKGROUND OF THE INVENTION

Biomedical materials which are particularly useful as contact lens materials fall into three general classifications; hydrogels, non-hydrophilic soft materials and rigid gas permeable materials.

The chemistries of contact lens hydrogels are almost completely described by polymer and copolymer systems comprised of either 2-hydroxyethylmethacrylate (HEMA) or N-vinyl-2-pyrrolidinone (NVP), or mixtures of HEMA and NVP. Minor components such as crosslinking agents are used in these systems to control tear strength, hydrolytic stability, modulus, etc. These hydrogel systems are generally well known and have been successful on a commercial basis, but they are not without shortcomings.

Polysiloxane based elastomers have also been known in the contact lens art for some time and have enjoyed limited commercial success. In general, the silicone chemistries involve vinyl functional end capped polysiloxane polymers.

Rigid gas permeable contact lens materials are generally copolymers formed from copolymerizing acrylic or methacryl functional monomers which contain siloxane functionalities and often also contain fluorine atoms.

The present invention provides a novel monomer chemistry to the art of biomedical device materials.

SUMMARY OF THE INVENTION

The present invention provides novel monomers useful in biomedical devices. These novel monomers have the general formula

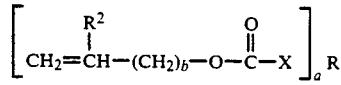

where b is 0 or 1, a is 1, 2, 3 or 4, $R^2$ is a monovalent alkyl radical and R is an organic radical. The novel monomers may be employed to produce novel copolymers useful as hydrogel, soft non-hydrogel and/or rigid gas permeable contact lens materials.

DETAILED DESCRIPTION OF THE INVENTION

The present invention is directed to new crosslinked copolymers which employ novel monomers also disclosed in this application. These novel copolymers are particularly useful as biomedical materials, and are especially useful in the area of contact lens applications. These new crosslinked copolymers, when used in contact lens applications, can produce a wide variety of types of contact lens materials ranging from hard, gas permeable lens materials; soft, hydrogel lens materials; to soft, non-hydrogel lens materials.

The novel monomers generally fall into the following classifications: a) hydrophilic monomers with the general formula

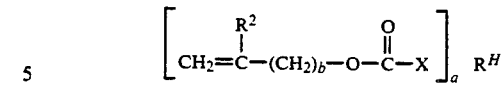

where b is 0 or 1; a is 1, 2, 3 or 4

X denotes —NH—, —S— or —O—; and $R^H$ denotes a hydrophilic moiety such as an organic radical with one or more amide hydroxyl, urea or carboxylic acid functionalities so that the monomer as a whole is relatively hydrophilic;

b) silicone containing monomers of the general formula

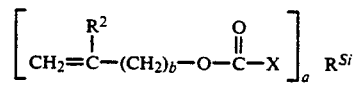

where a, b, and X are defined as above and $R^{Si}$ denotes a silicone containing organic radical;

c) non- or slightly hydrophilic monomers of the general formula

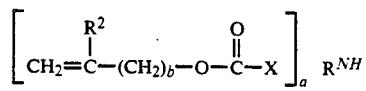

where a, b and X are as defined above and $R^{NH}$ denote a non-hydrophilic organic radical.

In general, there are no clear cut demarcations between any of the three classifications of contact lens materials. However, in general, hydrogel materials should have oxygen permeabilities with DK's greater than $20 \times 10^{-11}$ $cm^3 \times cm/sec. \times cm^2 \times mmHg$ (or DK units hereinafter) and preferably greater than 40 DK and most preferably greater than 60 DK. They should have a Young's modulus of elasticity in the range of 20 to 400 $g/mm^2$, preferably 50 to 200 $g/mm^2$ as measured by ASTM test method D 638. They should have tear strengths greater than 1 $g/mm^2$ and preferably greater than 5 $g/mm^2$ as measured by ASTM test method D 1938. Their water content should be between 10 to 80%, and preferably between 20 to 50%. The contact angle, which is a measurement of the wettability of the lens, should be less than 80° and should preferably be less than 40°. The protein uptake of hydrogel lenses or hydrogel lens materials should be less than or equivalent to that of PHEMA.

Soft, non-hydrogel materials should have at a minimum oxygen permeabilities equal to or greater than hydrogel materials. The water content should always be less than 10%, and preferably less than 5%. The modulus of elasticity should be between 20 and 5,000 $g/mm^2$ and preferably should be in the range of 50 to 250 $g/mm^2$. Contact angle less than 80° and preferably less than 40° and the tear strength (both initial and propagation) of this material should be in excess of 5 $g/mm^2$.

Properties of hard, gas permeable lens materials should be similar to that of the hydrogel and the soft, non-hydrogel materials. In addition, the glass transition temperature of such materials should be greater than 40° C. and preferably greater than 65° C. The modulus of the material should be greater than 50,000 $g/mm^2$ and preferably greater than 75,000 $g/mm^2$.

HYDROGEL MATERIALS

To prepare a soft, non-hydrogel material the following prepolymer formulations should be used: (a) between 25 and 90% of the prepolymer mixture should comprise a hydrophilic monomer portion. This portion will preferably comprise in part at least a hydrophilic monomer represented by the general formula

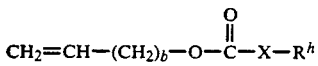

$$CH_2=CH-(CH_2)_b-O-\overset{O}{\underset{\|}{C}}-X-R^h$$

where b is 0 or 1 and X is —S—, —O—, or —NR$^3$— and R$^h$ denotes a relatively hydrophilic moiety. This hydrophilic monomer portion may also include at least one of the hydrophilic monomers chosen from the group consisting of wetting monomers N-vinyl-2-pyrrolidinone, 2-hydroxyethyl vinyl carbonate, 2-hydroxyethyl vinyl carbamate, 3-(2-pyrrolidinon-1-yl)-propyl vinyl carbonate, 2-(2-pyrrolidinon-1-yl)ethyl vinyl carbonate, N-(vinyloxycarbonyloxy)pyrrolidin-2,5-dione, N-[vinyloxycarbonyloxyethyl]pyrrolidin-2,5-dione, N-vinylacetamide, N-methyl-N-vinylacetamide, N,N-dimethyl vinyl carbamate, N,N-diethyl vinyl carbamate. These monomers may, of course, comprise only a portion of the hydrophilic monomer portion of prepolymer mix which can further be comprised of other hydrophilic monomers.

The hydrogel prepolymer formulation should also preferably contain (b) between 40 to 80 weight percent of a non- or weakly hydrophilic monomer as combination of monomers chosen from the group consisting of 3-[tris(tri-methylsiloxy)silyl]propyl vinyl carbonate, t-butyl vinyl carbonate, t-butyldimethylsiloxyethyl vinyl carbonate, 3-[tris(trimethylsiloxy)silyl]propyl vinyl carbamate, 3-(vinyloxycarbonylthio)propyl[tris(-trimethylsiloxy)]silane, 3-[tris(trimethylsiloxy)silyl]propyl allyl carbamate, t-butylphenyl vinyl carbamate. These non- or slightly hydrophilic monomers enhance the oxygen permeability of the final copolymer.

The hydrogel prepolymer compositions further comprise (c) between about 0.1 to 10% of a crosslinking agent, which may be chosen from a list of preferred crosslinking agents later disclosed in this application, or one of the crosslinking monomers known in the prior art as exemplified and/or taught in U.S. Pat. Nos. 4,060,678; 4,182,822; 4,267,295; 4,640,941 and/or 4,690,993.

The amount of hydrophilic monomer used to prepare the hydrogel material in the present invention is adjusted within the above limits to give a water content in the hydrated hydrogel of from about 5 to approximately 80% by weight. The non- or weakly hydrophilic monomer content is adjusted within the stated limits to maximize other desirable properties such as oxygen permeability, modulus and/or tear strength. The quantity of the crosslinking monomer used to produce a hydrogel material is adjusted to maximize desirable properties such as water content, modulus, lens strength, and also aids in the hydrolytically stability of the final material. In addition, UV absorbing monomers or tinting monomers may also be added to enhance the properties of the final material.

For instance, the following prepolymer formulations would produce hydrogel materials within the scope of the present invention.

| I. A. | 25-90 | wt % hydrophilic monomer, 2-hydroxyethyl vinyl carbamate; |
|---|---|---|
| B. | 10-30 | wt % non- or weakly hydrophilic monomer 3-N-[tris(trimethylsiloxy)silylpropyl] vinyl carbamate; and |
| C. | 0.1-10 | wt % crosslinker, 1,2-bis-(vinyloxy carbonyloxy)ethane. |
| II. A.i) | 25-90 | wt % hydrophilic monomer 2-hydroxyethyl vinyl carbamate; and |
| ii) | 25-90 | wt % hydrophilic monomer N-vinyl pyrrolidinone, where the combination of i and ii comprises between 25 to 90 wt % of the final prepolymer compositions. |
| B. | 10-90 | wt % of non-, or weakly hydrophilic monomer t-butyldimethylsiloxyethyl vinyl carbamate; and |
| C. | 0.1-10 | wt % crosslinker, α,ω-bis-(vinyloxycarbonyl) polyethylene glycol. |
| III. A. | 25-90 | wt % hydrophilic monomer, 3-(2-pyrrolidinon-1-yl)propyl vinyl carbamate; |
| B. | 10-30 | wt % weak or non-hydrophilic monomer, t-butyl vinyl carbamate; and |
| C. | 0.1-10 | wt % crosslinker, α,ω-bis-(vinyloxycarbonyl) polyethylene glycol. |

HARD, GAS PERMEABLE MATERIALS

Hard lenses are prepared using: (I) one or more of the non-hydrophilic monomers of the present invention; (II) a crosslinking agent; (III) a small amount of a wetting monomer; and (IV) optionally other agents such as strengthening agents or UV absorbing or dye monomers. The three main components are used in the following ratios; the non-hydrophilic monomer component (I) is used in amounts of about 60 to about 95 weight percent, the crosslinking monomer (II) in amounts from 0.1 to 10 weight percent, and the wetting monomer (III) in amounts from about 1 to 20 weight percent. The content of the crosslinking agent is chosen to provide a dimensionally stable lens material resistant to breakage and stress crazing. The amount of wetting monomer used is adjusted within limits to provide sufficient wetting characteristics so as to maintain a stable tear film while at the same time keeping a sufficiently low water content.

The non-hydrophilic monomers used to make the hard contact lens materials include one or more of the following monomers: 2,2,2-trifluoroethyl vinyl carbonate, 2,2,2-trifluoroethyl vinyl carbamate, 1,1,1,3,3,3-Hexafluoroprop-2-yl vinyl carbonate, 2,2,2-trifluoroethyl allyl carbonate, 2,2,2-trifluoro-1-phenylethyl vinyl carbonate, trimethylsilylmethyl vinyl carbonate, trimethylsilylethyl vinyl carbonate, 3-(trimethylsilyl)-propyl vinyl carbonate, t-butyldimethylsiloxyethyl vinyl carbonate, 3-[tris(trimethylsiloxy)silyl]propyl vinyl carbonate, 3-[tris-(trimethylsiloxy)silyl]propyl vinyl carbamate, 3-(vinyloxycarboxylthio) propyl-[tris(trimethylsiloxy)silane].

The crosslinking agents used preferably to make hard contact lens materials include crosslinking agents known in the prior art as taught in the U.S. patents referenced supra, but most preferably crosslinking agents chosen from the group consisting of crosslinking monomers represented by the formula

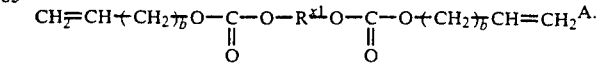

$$CH_2=CH+CH_2)_{\overline{b}}O-\underset{O}{\overset{\|}{C}}-O-R^{11}-O-\underset{O}{\overset{\|}{C}}-O+CH_2)_{\overline{b}}CH=CH_2 \quad A.$$

-continued

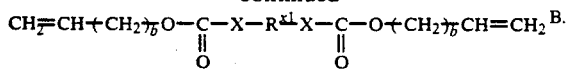

or

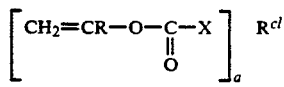    C.

wherein: X denotes —S—, —O—, or —NH— and at least one X denotes a —NH— in formula B; b is 0 or 1;

$R^{cl}$ denotes a multivalent organic radical and a is 2, 3, or 4; and $R^{x1}$ denotes a divalent organic radical.

The preferred crosslinkers includes:
1,5-bis-(vinyloxycarboxyloxy)-2,2,3,3,4,4-hexafluoropentane;
1,2-bis(vinyloxycarboxyloxy)ethane;
α,ω-bis(vinyloxycarbonyl)polyethylene glycol;
N,O-bis(vinyloxycarbonyl)ethanolamine;
2,2′-dimethyl-1,3-bis(vinyloxycarbonyloxy)propane;
α,ω-bis-(vinyloxycarbonyl)triethylene glycol;
2,2-dimethyl-N,N-bis(vinyloxycarbonyl)-1,3-propandiamine;
1,3-bis-[4-(vinyloxycarbonyloxy)but-1-yl] tetramethyldisiloxane;
N,N-bis-(vinyloxycarbonyl)-1,6-diaminohexane:

porated into the above formula from a synthetic perspective.

In general, $R^{NH}$ may be described by the following formulae:

$(CH_2)_n[Si((CH_2)_mCH_3)_3]$;
—$(CH_2)_nSi(OSi[(CH_2)_mCH_3]_3)_3$;

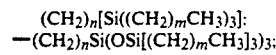

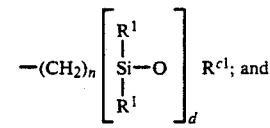

where $R^1$ denotes a monovalent organic radical such as an alkyl radical with 1 to 6 carbon atoms, or a fluoroalkyl radical with 1 to 6 carbon atoms;

$R^{cl}$ denotes

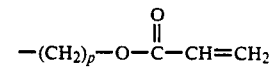

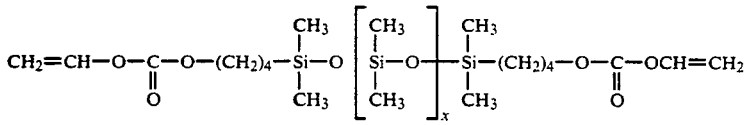

where X=25 on the average.

The wetting monomers useful in hard contact lenses include N-vinylpyrrolidinone, 2-hydroxyethylmethacrylate, itaconic acid, methacrylic acid, N,N-diethylacrylamide, N,N-diethyl vinyl carbamate, N,N-dimethyl vinyl carbamate, N-Methyl-N-Vinyl acetamide, and all hydrophilic monomers listed in the hydrogel section supra.

SOFT, NON-HYDROGEL MATERIALS

Soft, non-hydrogel contact lens materials with little or no water content can be prepared by polymerizing prepolymer mixtures with the following formulations: between 50 and 90 weight percent of non-hydrophilic monomers with the following general formula:

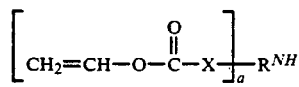

where X denotes either —O—, —S— or —NH—; and $R^{NH}$ represents an organic radical that is largely non-hydrophilic, and a is 1, 2, 3 or 4;
from 5 to about 25 weight percent of a hydrophilic monomer and between 0.1 and about 10% of a crosslinking monomer.

$R^H$, the largely non-hydrophilic moiety in the above formula, is typically a monovalent radical—but it may be multivalent. The main functional requirement is that it is largely non-hydrophilic, generally nonreactive to free-radical vinyl addition reactions and may be incorp is 1 to 6; and
d is 1–200, and
where n is 1, 2, 3 or 4, m is 0, 1, 2, 3, 4, or 5, or $R^{NH}$ denotes a partially or fully fluorinated alkyl, alkylaryl or aryl radical.

The non-hydrophilic monomers specifically include 3-[tris(trimethylsiloxy)silyl]propyl vinyl carbonate; 1,3-bis[4-(vinyloxycarbonyloxy)but-1-yl]tetramethyldisiloxane; 3-(trimethylsilyl)propyl vinyl carbonate; t-butyldimethylsiloxyethyl vinyl carbonate; trimethylsilylmethyl vinyl carbonate; trimethylsilylethyl vinyl carbonate; 2,2,2-trifluoroethyl vinyl carbonate; t-butyl vinyl carbonate; 3-[tris(trimethylsiloxy)silyl] propyl vinyl carbonate; 2,2,2-trifluoroethyl vinyl carbamate; 1,1,1,3,3,3-hexafluoro-2-propyl vinyl carbonate; 3-(vinyloxycarbonylthio)propyl-[tris(trimethylsiloxy)silane]; 3-[tris-(trimethylsiloxy)silyl]propyl vinyl carbamate; "V₂D₂₅", 2,2,2-trifluoro-1-phenylethyl vinyl carbonate; 1-adamantane vinyl carbonate, 1-adamantanemethyl vinyl carbonate, 1-adamantaneethyl vinyl carbonate; and 1-adamantane vinyl carbamate.

The hydrophilic monomers used to produce the proper wetting conditions in combination with the soft non-hydrogel materials are selected from hydrophilic monomers used in contact lenses in general, including N-vinyl lactams e.g., N-vinyl pyrrolidinone; hydroxyalkyl acrylates and methacrylates such as 2-hydroxyethyl methacrylate (HEMA) and preferably, the hydrophilic vinyl carbonates and vinyl carbamates disclosed in this application such as hydroxyethyl vinyl carbonate; N,N-dimethyl vinyl carbamate; or N-hydroxyethyl vinyl carbamate; N-[vinyloxycarbonyloxyethyl]pyrrolidin- 2,5-dione; and 3-(2-pyrrolidinon-1-yl)propyl vinyl carbonate.

Crosslinkers used for the soft, non-hydrogel contact lens materials include the crosslinkers known in the prior art such as methylene glycol dimethacrylate and divinylbenzene, but preferably are crosslinking agents described in the present application by formulas A, B and C.

The preferred non-hydrophilic monomers are the long chain siloxane monomers of the present invention such as the so-called "$V_2D_{25}$" monomers.

Some examples of soft non-hydrogel prepolymer formulations include:

I) 80 wt % $V_2D_{25}$;
   10 wt % N-vinyl-2-pyrrolidinone;
   5 wt % 2,2,2-trifluoroethyl vinyl carbonate; and
   5 wt % N-O-bis-(vinylcarbonyl)ethandamine.

II) 60 wt % 3-(trimethylsiloxy)propyl vinyl carbonate;
    30 wt % $\alpha,\omega$-bis(vinyloxycarbonyl) polyethylene glycol;
    5 wt % 1,1,1,3,3,3-Hexafluoroprop-2-yl vinyl carbonate; and
    5 wt % N-vinyl-N-methyl acetamide.

III) 25 wt % 3-(trimethylsilyl)propyl vinyl carbonate;
     64 wt % 3-[tris-(trimethylsiloxy)silyl]propyl vinyl carbamate;
     10 wt % N-vinylpyrrolidinone; and
     1 wt % 2,2-dimethyl-1,3-bis(vinyloxycarbonyloxy) propane.

IV) 20 wt % t-butyldimethylsiloxyethyl vinyl carbonate;
    70 wt % 3-[tris(trimethylsiloxy)silyl]propyl vinyl carbamate;
    9 wt % N-vinylpyrrolidinone; and
    1 wt % 2,2-dimethyl-1,3-bis(vinyloxycarbonyloxy) propane.

V) 20 wt % trimethylsilylethyl vinyl carbonate;
   69 wt % 3-[tris(trimethylsiloxy)silyl]propyl vinyl carbamate;
   10 wt % N-vinylpyrrolidinone; and
   1 wt % 2,2-dimethyl-1,3-bis(vinyloxycarbonyloxy) propane.

The copolymers of the present invention are formed by way of a free radical polymerization the details of which are generally known in the art. In general, the various comonomers are chosen and combined, as required to form the desired final copolymers, and a free radical catalyst is added to the mixture. The mixture is then polymerized to form the desired copolymer.

Free radical catalysts are known in the art and are mostly of two general types: heat initiated free radical catalysts, and photoinitiated free radical catalysts, more specifically, ultraviolet radiation initiated free radical catalysts. Heat initiated catalysts include peroxides such as 2,5-dimethyl-2,5-bis(2-ethylhexanoylperoxy) hexane (Lupersol 256 TM Pennwalt Chemicals), bisisopropylperoxydicarbarate, acetylperoxide, lauroyl peroxide or benzoyl peroxide, photoinitiators include compounds such as 2-hydroxy-2-methyl-1-phenylpropan-1-one (Darocur TM, EM Chemicals), and the like.

Diluents may be employed in the process of polymerizing the copolymers of the present invention in order to modify the resultant physical characteristics of the finished copolymer. For instance, the comonomer mixture used to produce a hydrogel like material may also include a portion of methylethylketone. In general, the amount of diluent used should be less than 50 wt. %. In most cases, the diluent content will be less than 30 wt. %. In a particular copolymer system, the actual limit will be dictated by the solubility of the various comonomers in the diluent. In order to produce an optically clear copolymer, it is important that a phase separation does not occur between the comonomers and the diluent, or the diluent and the final copolymer.

Furthermore, as a practical matter, the maximum amount of diluent which may be used will depend on the amount of swelling the diluent causes the final copolymers. Excessive swelling will or may cause the copolymer to collapse when the diluent is replaced with water upon hydration.

Suitable diluents include ethyleneglycol; glycerine; liquid polyethyleneglycol; alcohols; alcohol/water mixtures; ethylene oxide/propylene oxide block copolymers; low molecular weight linear polyhydroxyethylmethacrylates; glycol esters of lactic acid; formamides; ketones; dialkylsulfoxides; butyl carbitol; and the like.

These novel copolymers in general are made from polymerizing mixtures comprising:

a) from 1 to 99 wt. % of a base monomer of the general chemical formula

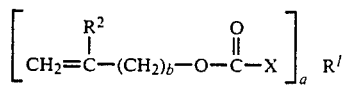

wherein:

X denotes an —O—, —S—, or —NR$^3$— divalent radical;

R$^1$ denotes an organic radical;

R$^2$ denotes —H or —CH$_3$;

R$^3$ denotes —H, or a monovalent alkyl radical;

a is 1, 2, 3, or 4; and b is 0 or 1.

b) from 0.1 to 20 wt. % of a crosslinking agent known in the biomedical material art, or a novel crosslinker represented by the chemical formulae:

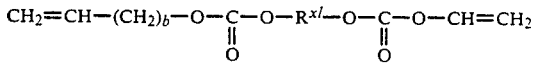

or

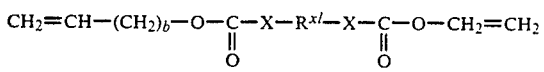

or

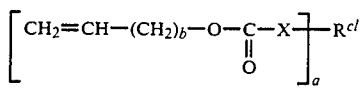

wherein: X is —O— or —NH— with at least one X being —NH—; R$^{cl}$ denotes a multivalent organic radical, b is 0 or 1, and a is 2, 3 or 4.

These copolymers may also contain further additives such as wetting agents, tints, dyes, strengthening agents and the like to tailor specific material properties as desired.

The copolymers of the present invention are useful as biomedical devices, and in particular, are well suited as contact lens materials. The copolymers can be formed into contact lenses by many of the techniques known in the art to be useful in contact lens production. For instance, prepolymer mixtures containing heat initiated free radical catalysts can be placed in polypropylene tubes which are then heat cured over time to form copolymeric rods which are then cut to form button shaped articles. These button shaped articles can then be lathed into contact lenses.

Alternately, the prepolymer mixture can be molded per the methods disclosed in U.S. Pat. Nos. 4,085,459 or 4,197,266. Spin casting techniques may also be used with the present materials and such methods as described in U.S. Pat. Nos. 3,408,429 and 3,496,254 can be so adopted to be useful with the present copolymers.

SYNTHESIS OF MONOMERS

Part I—Synthesis of Hydroxalkyl Monomers Useful as Hydrogel Base Monomers and Wetting Agents

1.0 2-Hydroxyethyl Vinyl Carbonate $C_6H_8O_4$

To a 1000 mL 3-neck round bottom flask fitted with a magnetic stirrer, condenser, $N_2$ blanket, thermometer, and a dropping funnel 5.0 g (81.66 mmol) of ethylene glycol. 7.12 g (90.0 mmol) of pyridine and 500 mL of chloroform were added. To this reaction mixture 8.779 g (81.66 mmol) of vinyl chloroformate was added over 20 minutes. The reaction mixture was stirred for 16 hours. The volume of the mixture was reduced to 75 mL on a rotary evaporator and the residue washed with 100 mL of 2N HCl. The aqueous phase was set aside. The organic phase was dried over magnesium sulfate. The solvent was removed on a rotary evaporator and the resulting oil was purified by chromatography (silica gel, gradient starting with 60% cyclochexane 40% chloroform) to give an oil. The 2N HCl wash was saturated with sodium chloride and extracted three times with 50 mL chloroform. The combined chloroform extracts were dried with magnesium sulfate and flash evaporated to an oil. The oils combined to give 2.3 g (17.4mmol, 21.3%) of a light yellow oil. FTIR (neat, capillary) 3500.56, 3477.38, 3379.94, 2960.20, 1805.29, 1753.69, 1650.79, 1558.65, 1540.44, 1506.71, 1481.33, 1455.89, 1388.72, 1373.25, 1299.19, 1244.25, 1154.19, 1067.30, 1015.59, 995.52, 969.77, 944.14, 913.44, 875.08, 859.65, 779.15, 717.53, 684.06, 666.45, 649.43. NMR ($CDCl_3$) δ 6.83-7.177 (1H,m), 4.56-5.0 (2H,m), 4.13-4.37 (2H,m), 3.70-3.93 (2H,m), 3.07-3.43 (1H,s). The instrumental analyses were consistent with a compound represented by the following formula:

$$CH_2=CH-O-\underset{\underset{O}{\|}}{C}-O-CH_2CH_2OH$$

1.1 2-Hydroxyethyl Vinyl Carbamate $C_5H_9NO_3$

To a 500 mL 3-neck round bottom flask fitted with a magnetic stirrer, condenser, $N_2$ blanket, thermometer, and dropping funnel 20.0 g (327.4 mmol) of ethanolamine and 200 mL of chloroform were added. 17.44 g (163.7 mmol) of vinyl chloroformate was added to the mixture over 20 minutes raising the temperature to 53° C. The reaction mixture was cooled to room temperature and stirred for 16 hours. The resolution precipitate was removed by filtration. The filtrate was evaporated to remove solvent and the residual oil was distilled (125° C.±5° C. 0.89 Torr) to give 21.2 g (161.7 mmol, 98.8%) of a light yellow oil. FTIR (neat, capillary) 3314.69, 2940.08, 2885.15, 1705.86, 1648.26, 1522.62, 1458.28, 1432.05, 1403.96, 1363.49, 1339.67, 1294.21, 1244.90, 1160.44, 1116.66, 1059.67, 1010.44, 947.03, 921.01, 861.00, 768.57, 731.09, NMR ($CDCl_3$) δ 6.90-7.23 (1H,m), 5.76-6.3 (1H,s), 4.26-4.83 (2H,m), 3.50-3.93 (3H,m), 3.07-3.47 (2H,m). The spectral analyses were consistent with the following chemical structure.

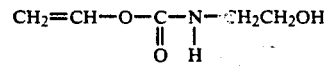

1.2 N-(Vinyloxycarbonyloxy)-pyrrolidin-2.5-dione

To a 500 mL 3-neck round bottom flask fitted with a mechanical stirrer, condenser, nitrogen blanket, dropping funnel, ice-saltwater bath, and thermometer were added 10.0 (87.0 mmol) of N-hydroxy succinimide, 6.9 g (87.0 mmol) of pyridine, and 100 mL tetrahydrofuran was added. To the reaction mixture 9.25 g (87.0 mmol) of vinyl chloroformate was added so that the temperature remained below 10° C. After stirring at room temperature for 18 hours the reaction mixture was washed with 100 mL 2N HCl, and 100 mL 2N NaOH. The organic phase was dried over magnesium sulfate. The solvent was removed on a rotary evaporator and the resulting liquid chromatographed (silica gel, chloroform) to yield 10.0 g (54.0 mmol, 62.1% yield) of an oil. FTIR (neat, capillary) 3516.50, 3132.04, 3099.40, 3003.94, 2960.21, 1830.80, 1823.25, 1792.36, 1734.05, 1671.98, 1653.62, 1646.30, 1429.97, 1380.77, 1368.60, 1306.35, 1260.89, 1241.83, 1201.12, 1162.09, 1154.49, 1134.29, 1087.59, 1049.93, 1005.21, 990.18, 948.77, 941.86, 908.06, 897.29, 892.42, 812.37, 769.04, 756.85, 724.90, 707 81. NMR ($CDCl_3$) 6.73-7.09 (1H,q), 4.61-5.24 (2H,m), 2.78 (4H,S).

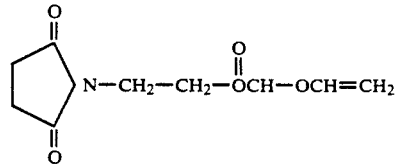

1.3 N-(Vinyloxycarbonyloxyethyl)pyrrolidin-2,5-dione

To a 500 mL 3-neck round bottom flask fitted with a mechanical stirrer, condenser, nitrogen blanket, dropping funnel, ice-saltwater bath, and thermometer were added 5.0 (35.0 mmol) of N-(2-hydroxyethyl) succinimide, 2.8 g (35.0 mmol) of pyridine, and 100 mL chloroform. To the reaction mixture was added 3.7 g (35.0 mmol) of vinyl chloroformate so that the temperature remained below 10° C. After stirring at room temperature for 18 hours the reaction mixture was washed with 100 mL 2N HCl and 100 mL 2N NaOH. The organic phase was dried over magnesium sulfate. The solvent was removed on a rotary evaporator and the resulting red liquid chromatographed (silica gel, chloroform). The recovered oil totaled 3.0 g (14.1 mmol, 40.2% yield). FTIR (neat, capillary) 1755.10, 1694.90, 1648.77, 1427.00, 1396.38, 1366.15, 1329.97, 1298.34, 1239.58, 1185.85, 1152.26, 1111.20, 1085.92, 1024.25, 1005.00, 946.53, 894.87, 882.46, 848.52, 818.51, 778.99, 700.00, 661.32. NMR ($CDCl_3$) 6.50-6.83 (1H,q), 4.13-4.66 (2H,m), 3.93-4.13 (2H,m), 3.33-3.66 (2H,m), 2.41 (4H,S).

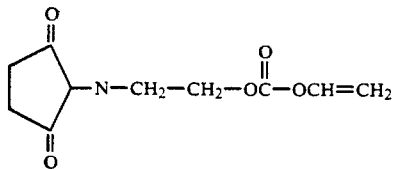

Part II—Synthesis of Pyrrolidinone Moiety Containing Monomers

2.0 3-(2-Pyrrolidinon-1-yl)propyl Vinyl Carbonate $C_{10}H_5NO_4$

To a 250 mL 1-neck round bottom flask fitted with a magnetic stirrer, dropping funnel, and ice bath, 12.5 g (87.3 mmol) of N-(3-hydroxypropyl)-2-pyrrolidinone, 7.6 g (96.0 mmol) of pyridine and 100 mL of chloroform were added. To the ice cold reaction mixture 9.3 g (87.3 mmol) of vinyl chloroformate was added over 5 minutes. After 5 minutes a precipitate formed. The reaction mixture was adsorbed on silica gel then purified by chromatography (silica gel, methylene chloride) to give 17.3 g (81.1 mmol, 93.0%) of a straw colored oil. FTIR (neat, capillary) 2963.22, 1754.09, 1676.89, 1646.83, 1566.02, 1494.64, 1463.44, 1425.05, 1396.11, 1357.91, 1336.92, 1296.25, 1239.43, 1152.41, 1085.28, 1024.06, 998.00, 946.11, 882.00, 761.74, 737.53, 697.39, 651.25. NMR (CDCl$_3$) 6.82–7.17 (1H,m), 4.40–4.96 (2H,m), 4.06–4.28 (2H,m), 3.24–3.47 (4H,m), 1.68–2.56 (6H,m). The spectral analyses were consistent with the following chemical structure.

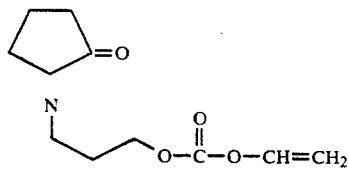

2.1 2-(2-Pyrrolidinon-1-yl)ethyl Vinyl Carbonate $C_9H_{13}NO_3$

To a 250 mL 1-neck round bottom flask fitted with a magnetic stirrer, dropping funnel, and ice bath, were added 10.0 g (77.4 mmol) of N-2-(hydroxyethyl) pyrrolidinone, 6.7 g (84.7 mmol) of pyridine and 100 mL of chloroform. To the ice cold solution 8.3 g (78.0 mmol) of vinyl chloroformate was added. The mixture was stirred for 30 minutes, forming a precipitate. The reaction mixture was chromatographed (silica gel, methylene chloride) 90% toluene 10%) to give 8.3 g (41.7 mmol, 53.9%) of a light yellow oil. FTIR (neat, capillary) 2962.91, 1754.66, 1679.48, 1646.22, 1494.64, 1462.88, 1438.22, 1424.48, 1393.77, 1368.15, 1327.55, 1286.44, 1237.47, 1152.71, 1113.47, 1085.63, 1046.25, 1018.86, 979.70, 946.17, 894.98, 877.43, 853.32, 779.37, 735.01, 697.06, 650.86. NMR (CDCl$_3$) δ 6.84–7.17 (1H,m), 4.45–5.01 (2H,m), 4.18–4.35 (2H,m), 3.32–3.62 (4H,m), 1.70–2.50 (4H,m). Spectral analyses were consistent with the proposed chemical structure.

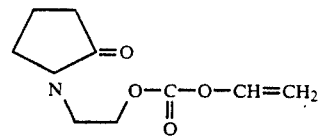

Part III—Synthesis of Haloalkyl Containing Monomers

3.0 2,2,2-Trifluoroethyl Vinyl Carbonate $C_5H_5O_3$

To a 2 liter 4-neck round bottom flask fitted with a mechanical stirrer, condenser, nitrogen blanket, thermometer, ice-water bath, and dropping funnel 47.45 g (0.6 moles) of pyridine and 600 mL of methylene chloride was added. The mixture was cooled to between 5° and 8° C., a white precipitate formed. Then 60.02 g (0.6 moles) of 2,2,2-trifluoroethanol was added. The reaction was warmed to room temperature for 20 hours. A precipitate remained but had changed texture. The organics were washed thrice with 200 mL 2N HCl, once with saturated NaCl then twice with 200 mL 2N NaOH. The organics were dried over magnesium sulfate then distilled through an 8 inch vigreux to give a colorless oil which had the following characteristics (bp 107° C., 760.0 Torr), 66.1 g (0.389 mole, 64.8%). FTIR (neat, capillary) 2985.97, 1790.03, 1653.80, 1447.48, 1412.48, 1386.07, 1316.41, 1255.45, 1185.52, 1157.41, 1098.83, 1082.16, 995.88, 962.47, 941.20, 910.72, 881.10, 777.15, 694.53, 665.95. NMR (CDCl$_3$) δ 6.88–7.26 (1H,m), 4.33–5.20 (4H,m). The spectral analyses were consistent with the following structure.

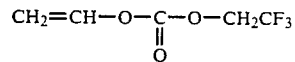

3.1 2,2,2-Trifluoroethyl Vinyl Carbamate $C_5H_6F_3NO_2$

To a 1 L 3-neck round bottom flask fitted with a mechanical stirrer, condenser, thermometer, and ice water bath 32.11 g (406.0 mmol) of pyridine and 450 mL of ether was added. After the temperature was stabilized at 12.5° C.±2.5° C. 21.6 203.0 mmol of 2,2,2-trifluoroethyl amine hydrochloride was added in one portion, then the reaction was stirred to room temperature for 18 hours. The organics were washed twice with 300 mL 2N HCl, once with 100 mL 2N NaOH, then dried with magnesium sulfate. The solvent was removed on a rotary evaporator and the resulting oil was distilled at (70° C., 30 Torr) to give a white crystalline solid (mp 43°–44° C.) 6.8 g (40.2 mmol, 21.8%). FTIR (SRATR) 3325.47, 2957.22, 2921.47, 2852.61, 1722.84, 1651.46, 1540.06, 1458.41, 1427.89, 1396.91, 1299.01, 1281.24, 1237.54, 1150.23, 1121.40, 1023.84, 956.16, 946.33, 871.75, 830.76, 771.03, 669.23. NMR (CDCl$_3$) 6.95–7.27 (1H,m), 5.07–5.66 (1H,b), 4.33–4.86 (2H,m), 3.50–4.13 (2H,m).

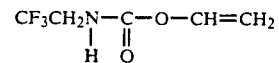

3.2 1,1,1,3,3,3-Hexafluoroprop-2-yl Vinyl Carbonate C₆H₄F₆O₃

To a 1000 mL 3-neck round bottom flask fitted with a mechanical stirrer, condenser, nitrogen blanket, thermometer, dropping funnel, and ice-water bath 43.50 g (550.0 mmol) of pyridine and 600 mL methylene chloride was added. After cooling to 5° C.±2° C. 53.3 g (500.0 mmol) of vinyl chloroformate was added while maintaining the temperature. A white precipitate formed immediately. When the addition was complete, 92.4 g (550.0 mmol) 1,1,1,3,3,3-hexafluoro-2-propanol was added. The reaction was stirred at room temperature for 18 hours. The organics were washed twice with 500 mL ice cold 2N HCl, once with 500 mL ice-cold saturated NaCl, dried over magnesium sulfate, and then distilled through an 8 inch vigreux to give a colorless oil (bp 97° C., 760.0 Torr), 21.5 g (90.3 mmol, 18.1%). FTIR (neat, capillary) 2980.79, 1782.53, 1654.02, 1383.67, 1363.76, 1309.32, 1296.81, 1252.69, 1196.39, 1098.72, 1021.71, 936.52, 922.78, 905.85, 887.05, 866.80, 773.96, 712.08, 689.17. NMR (CDCl₃) δ 6.83–7.23 (1H,m), 5.26–5.86 (1H,m), 4.56–5.23 (2H,m).

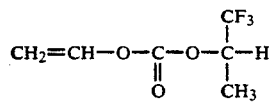

3.3 2,2,2-Trifluoro-1-phenylethyl Vinyl Carbonate C₁₁H₉F₃O₃

To a 250 mL round bottom flask fitted with a mechanical stirrer, condenser, nitrogen blanket, thermometer, ice-water bath, and dropping funnel 12.5 g (71.0 mmol) of 1-phenyl-2,2,2-trifluoroethanol, 7.6 g (71.0 mmol) triethylamine and 100 mL ethylether was added. After cooling to 12.5° C.±3° C., 7.6 g (71.0 mmol) of vinyl chloroformate was added while maintaining the temperature. The reaction mixture was filtered to remove triethylamine-hydrochloride. The filtrate was washed twice with 2N HCl, once with distilled water then dried with magnesium sulfate. The solvent was removed on a rotary evaporator and the crude oil was distilled to give a colorless oil (bp 90° C., 4.5 Torr), 12.2 g (49.6 mmol, 69.8%). FTIR (neat, capillary) 1800.23, 1767.51, 1733.45, 1653.30, 1558.52, 1499.70, 1458.25, 1383.98, 1355.92, 1312.00, 1301.65, 1273.65, 1241.93, 1208.55, 1182.79, 1157.35, 1131.65, 1088.2, 1031.72, 998.12, 938.91, 928.82, 913.17, 877.34, 849.19, 776.46, 760.96, 696.97. NMR (CDCl₃) δ 7.30 (5H,S), 6.76–7.03 (1H,m), 5.66–6.00 (1H,m), 4.36–9.33 (2H,m).

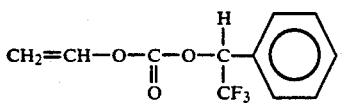

Part IV—Silicon Containing Monomers

4.0 Trimethylsilylmethyl Vinyl Carbonate C₇H₁₄O₃Si

To a 250 mL 3-neck round bottom flask fitted with a magnetic stirrer, condenser, nitrogen blanket, dropping funnel, and thermometer was added 3.8 g (48.0 mmol) of pyridine then 50 mL of chloroform. The mixture was cooled to 12° C.±3° C. with an ice-water bath. Next 5.0 g (48.0 mmol) of trimethylsilyl methanol then 5.1 g (48.0 mmol) of vinyl chloroformate were slowly added so that the temperature was maintained. The cooling bath was removed and the reaction mixture was stirred for one hour. The organics were washed four times with 100 mL 2N HCl, twice with distilled water and then dried over magnesium sulfate. The solvent was removed under reduced pressure to give an oil. The oil was passed through silica gel to give 4.8 g (27.56 mmol, 57.1%) of colorless oil. FTIR (neat, capillary) 2958.37, 1754.67, 1648.09, 1420.24, 1383.80, 1302.02, 1226.95, 1155.20, 1085.49, 944.10, 913.47, 840.69, 779.53, 735.76, 669.81, 668.88. NMR (CDCl₃) δ 6.73–7.07 (1H, m), 4.25–4.85 (2H,m), 3.73 (2H,S), 0.00 (9H,S).

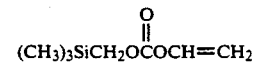

4.1 Trimethylsilylethyl Vinyl Carbonate C₈H₁₆O₃Si

To a 250 mL 3-neck round bottom flask fitted with a magnetic stirrer, condenser, nitrogen blanket, dropping funnel, and thermometer was added 6.69 g (85.0 mmol) of pyridine then 100 mL of chloroform. The reaction was cooled to 12° C.±3° C. with an ice-water bath. Next 10.0 g (85.0 mmol) of trimethylsilyl ethanol and 9.01 g (85.0 mmol) of vinyl chloroformate were added so that the temperature was maintained. The cooling bath was removed and the reaction mixture was stirred for one hour. The organic phase was washed four times with 100 mL 2N HCl, twice with distilled water then dried over magnesium sulfate. The solvent was removed under reduced pressure to give an oil. The oil was passed through silica gel to give 6.0 g (31.9 mmol, 37.5%) of colorless oil. FTIR (neat, capillary) 2955.56, 1754.65, 1648.64, 1456.39, 1414.83, 1388.75, 1298.51, 1239.97, 1178.60, 1154.64, 1082.23, 1061.84, 1043.84, 1026.67, 943.56, 918.45, 856.41, 832.97, 784.30, 767.03, 694.35, 663.60. NMR (CDCl₃) 6.80–7.13 (1H,m), 4.42–4.91 (2H,m), 4.03–4.40 (2H,m), 0.87–1.15 (2H,m), 0.00 (9H,S).

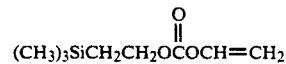

4.2 3-(Trimethylsilyl)propyl Vinyl Carbonate C₉H₁₈O₃Si

To a 500 mL 3-neck round bottom flask fitted with a magnetic stirrer, condenser, nitrogen blanket, thermometer, and dropping funnel was added 25.0 g (189 mmol) of trimethylsilyl-3-propanol, 16.45 g (208 mmol) of pyridine and 175 mL of toluene. In one portion, 22.1 g (208 mmol) of vinylchloroformate was added to the reaction mixture. An exotherm to 73° C. was noted. The mixture was stirred for 3 hours at room temperature then at 50° C. for 2 hours then at room temperature for 18 hours. The organic phase was washed with 250 mL 2N HCl then with 250 mL 2N NaOH₃ and the organic phase dried with magnesium sulfate. The solvent was removed on a rotary evaporator and the resulting oil distilled to give a colorless oil (bp 115° C., 35 Torr), 14.7 g (7.27 mmol, 38.5%). FTIR (neat, capillary) 2955.00, 2898.21, 1758.60, 1649.23, 1468.16, 1453.00, 1439.73, 1414.72, 1391.72, 1350.50, 1298.51, 1239.70, 1190.91, 1157.19, 1090.25, 1057.10, 1031.32, 995.02, 944.19, 902.70, 856.58, 833.86, 782.42, 753.39, 691.98. NMR (CDCl$_3$) δ 6.86–7.18 (1H,m), 4.36–4.88 (2H,m), 3.96–4.18 (2H,m), 1.40–1.91 (2H,m), 0.36–0.65 (2H,m), 0.00 (9H,S).

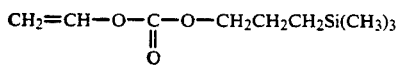

4.3 t-Butyldimethylsiloxyethyl Vinyl Carbonate C$_{11}$H$_{22}$O$_4$Si

To a 500 mL 3-neck round bottom flask fitted with a magnetic stirrer, condenser, nitrogen blanket, thermometer, dropping funnel, and ice-water bath was added 19.8 g (112.3 mmol) of tert-butyldimethylsiloxy ethyleneglycol, 9.8 g (112.3 mmol) of pyridine and 300 mL of ether. After cooling to 10° C.±5° C., 11.96 g (112.3 mmol) of vinyl chloroformate was added dropwise so that the temperature was maintained. A precipitate was formed and the reaction was stirred to room temperature over 16 hours. The organic phase was washed twice with 100 mL 2NHCl, twice with 100 mL 2N NaOH then dried over magnesium sulfate. The solvent was flashed off on a rotary evaporator and the resulting oil was passed through a short chromatography column (silica gel, chloroform) to give 26.9 g (109.2 mmol, 97.2%) of clear liquid. FTIR (neat, capillary) 2955.19, 2929.89, 2857.80, 1759.76, 1651.09, 1743.16, 1463.41, 1386.69, 1373.24, 1362.91, 1339.85, 1298.68, 1239.45, 1159.95, 1136.18, 1110.98, 1084.87, 1026.06, 1005.69, 944.16, 902.24, 869.65, 828.32, 812.16, 774.36, 714.82, 682.03, 661.17. NMR (CDCl$_3$)δ 6.78–7.12 91H,m), 4.35–4.93 (2H,m), 4.03–4.26 (2H,m), 3.60–3.83 (2H,m) 0.82 (9H,S), 0.00 (6H,S).

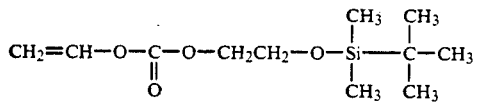

4.4 3-[Tris(trimethylsiloxy)silyl]propyl vinyl Carbonate C$_{15}$H$_{36}$O$_6$Si$_4$ To a 100 mL 3-neck round bottom flask fitted with a magnetic stirrer, dropping funnel, thermometer, and condenser, was added 9.5 g (38.0 mmol) of 3-(trimethoxysilyl) propyl vinylcarbonate and 16.6 g (125.3 mmol) of trimethylsilylacetate. To this reaction mixture was added 3.45ml of a catalyst prepared by mixing 23.8 g (242.7 mmol) of sulfuric acid, 11.6 g (251.8 mmol) of absolute ethanol and 16.5 g (916.0 mmol) of water. The addition took twenty minutes and an 8° C. exotherm was noted. The reaction was allowed to stir at room temperature for 16 hours and was then diluted with 200 mL of chloroform, washed twice with 100 mL 2N NaOH, and dried over magnesium sulfate. The solvent was removed on a rotary evaporator to give 15.3 g of crude oil. Following chromatography (silica gel, 80% Heptane, 20% methylene chloride) the oil was distilled (bp 125° C., 0.8 Torr), 3.5 g (8.24 mmol, 21.7%). FTIR (neat, capillary) 2958.06, 2898.76, 1762.06, 1650.84, 1543.76, 1393.82, 1319.20, 1298.62, 1245.44, 1199.11, 1160.19, 1041.77, 975.14, 946.32, 833.42, 782.42, 753.08, 714.62, 686.73, 658.57. NMR (CDCl$_3$) 6.71–7.10 (1H,m), 4.28–4.83 (2H,m), 3.85–4.08 (2H,m), 1.36–1.85 (2H,m), 0.23–0.50 (2H,m), 0.00 (27H,S).

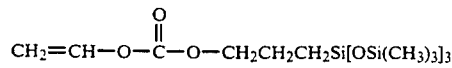

4.5 3-[Tris(trimethylsiloxy)silyl]propyl Vinyl Carbamate C$_{15}$H$_{17}$NO$_5$Si$_4$ To a 100 mL 3-neck round bottom flask fitted with a magnetic stirrer, and dropping funnel was added 5.0 g (14.1 mmol) of 3-amino propyl(trimethylsiloxy)silane, 1.23 g (15.6 mmol) of pyridine and 50 mL of chloroform. Five minutes after adding 1.5 g (14.1 mmol) of vinyl chloroformate, an exotherm resulted. The reaction mixture was checked by gas chromatography after 10 minutes and the starting amine was consumed. The organic phase was washed once with 100 mL 2N HCl then dried with magnesium sulfate. The solvent was removed on a rotary evaporator to afford 5.8 g of crude brown oil. Following chromatography (silica gel, 50% heptane 40% methylenechloride), 5.0 g (11.8 mmol, 83.3%) of colorless oil (bp 130° C., 0.8 Torr) was obtained. FTIR (neat, capillary) 2957.80, 1751.43, 1718.38, 1648.64, 1529.69, 1445.45, 1407.29, 1293.71, 1249.76, 1195.93, 1165.08, 1041.17, 972.34, 951.33, 833.18, 752.97, 715.26, 686.34, 656.45. NMR (CDCl$_3$) 6.91–7.26 (1H,m), 4.16–4.66 (3H,m), 2.80–3.20 (2H,m), 1.20–1.71 (2H,m), 0.20–0.48 (2H,m), 0.00 (27H,S).

$$CH_2=CH-O-\underset{\underset{O}{\|}}{C}-\underset{\underset{}{|}}{\overset{H}{N}}-CH_2CH_2CH_2Si[OSi(CH_3)_3]_3$$

4.6 3-(Vinyloxycarbonylthio)propyl-[tris(trimethylsiloxy) silane]

To a 500 mL 1-neck round bottom flask fitted with a magnetic stirrer and a condenser, was added 33.0 g (123.9 mmol) of 3-(trimethoxysilyl) propyl thio vinyl carbonate and 81.9 g (619.2 mmol) of trimethyl silyacetate. With rapid stirring, 11.3 mL of an acid catalyst prepared by mixing 23.8 g (242.7 mmol) of sulfuric acid, 11.6 g (251.8 mmol) of absolute ethanol and 16.5 g (916.0 mmol) of water) unsaturated. A vigorous exotherm was noted. After 30 minutes the reaction mixture was dissolved in 300 mL chloroform and washed twice with 100 mL of 2N NaOH and dried over magnesium sulfate. The solvent was removed on a rotary evaporator and the resulting oil was chromatographed (silica gel, chloroform). The product was distilled (160° C., 0.8 Torr) to afford 25.5 g (57.86 mmol, 46.7%) of a colorless oil. FTIR (neat, capillary) 2957.71, 1720.75, 1645.91, 1250.16, 1136.24, 1113.53, 1098.48, 1038.97, 944.04, 912.93, 833.12, 751.61, 717.00, 686.49, 658.44. NMR (CDCl$_3$) δ6.95–7.32 (1H,m), 4.32–4.85 (2H,m), 2.63–2.88 (2H,m), 1.62–1.88 (2H,m), 0.28–0.62 (2H,m), 0.00 (27,S).

$$CH_2=CH-O-\underset{\underset{O}{\|}}{C}-S-CH_2CH_2CH_2Si[OSi(CH_3)_3]_3$$

4.7 3-[Tris(trimethylsiloxy)silyl]propyl Allyl Carbamate

To a 100 mL 3-neck round bottom microware flask fitted with a magnetic stirrer, condenser, N$_2$ blanket, and dropping funnel, was added 4.8 g (13.57 mmol) of 3-aminopropyltris(trimethylsiloxy) silane, 1.18 g (15.0 mmol) of pyridine and 50 mL of chloroform. To the reaction mixture, 1.65 g (13.6 mmol) of allyl chloroformate was added dropwise resulting in a pink color and an exotherm to near reflux. After 72 hours, the light yellow organic phase was washed once with 100 mL 2N HCl, once with 100 mL 2N NaOH, and then dried with magnesium sulfate. The solvent was removed on a rotary evaporator to afford an oil. Following chromatography (silica gel, CHCl₃), the product was distilled (bp 123° C., 0.7 Torr) to give 4.0 g (9.1 mmol, 66.6%) of a colorless oil. FTIR (neat, capillary) 2957.56, 1702.88, 1527.57, 1445.45, 1409.33, 1249.69, 1195.48, 1039.35, 993.11, 928.34, 833.37, 753.07, 717.02, 686.29, 656.22. NMR (CDCl₃) δ 5.52–6.13 (1H,m), 4.88–5.34 (2H,m), 4.36–4.80 (3H,m), 2.83–3.22 (2H,m), 1.16–2.00 (2H,m), 0.16–0.47 (2H,m), 0.00 (27H,S).

mmol) of sodium bicarbonate was added which resulted in foaming. After 24 hours a small amount of black solids formed. The reaction mixture was filtered through 20.0 g of activated F20 alumina to give a light yellow oil. The oil was heated at 80° C. at 0.25 Torr for 3½ hours to remove volatiles, giving 13.4 g (5.90 mmol, 49.4%) of a light yellow oil. FTIR (neat, capillary) 2960.92, 1763.97, 1255.70, 1219.52, 1160.33, 1008.42, 946.68, 864.60, 782.03, 700.22, 686.57, 661.36. NMR (CDCl₃) δ 6.83–7.16 (2H,m), 4.36–4.93 (4H,m), 4.00–4.20 (4H,m), 1.16–1.91 (8H,m), 0.32–0.62 (4H,m), 0.000 (168,S).

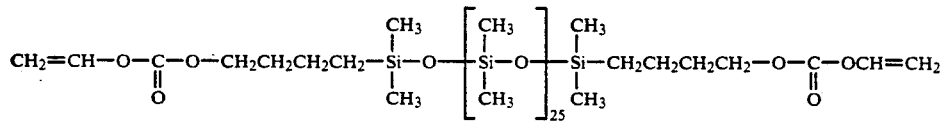

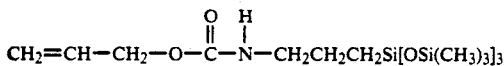

4.8
1,3-Bis[4-(vinyloxycarbonyloxy)but-1-yl]-tetramethyl disiloxane

To a 500 mL 3-neck round bottom flask fitted with a magnetic stirrer, condenser, N₂ blanket, dropping funnel, and thermometer, was added 10.0 g (35.9 mmol) of 1,3-bis (4-hydroxylbutyl) tetramethylsiloxane, 6.24 g (78.9 mmol) of pyridine and 100 mL of chloroform. Next, 7.64 g (71.8 mmol) of vinyl chloroformate was added to the mixture dropwise producing an exotherm to 54° C. The reaction mixture was cooled to room temperature and stirred for 19 hours. The organic phase was washed twice with 100 mL 2N HCl, twice with 100 mL 2N NaOH, then dried over magnesium sulfate. The solvent was removed on a rotary evaporator and the resulting oil was chromatographed (silica gel, chloroform) to give 13.22 g (31.6 mmol, 88.1%) of a light yellow oil. FTIR (neat, capillary) 2955.52, 1756.77, 1650.72, 1456.32, 1394.01, 1296.50, 1237.62, 1185.46, 1157.25, 1043.91, 990.80, 944.43, 868.86, 836.27, 781.65, 701.78. NMR (CDCl₃) δ 6.80–7.13 (2H,m), 4.37–4.92 (4H,m), 4.00–4.20 (4H,m), 1.55–1.88 (8H,m), 0.33–0.60 (4H,m), 0.00 (12H,S).

4.10 -Methyl-N-Tris(trimethylsiloxy)silylpropyl vinyl carbamate

To a 300 mL 3-neck round bottom flask fitted with a mechanical stirrer, condenser, nitrogen blanket, dropping funnel was added 514.2 g (3.186 mmols) of hexamethyldisilazane. To the reaction flask was added 675 mL of methanol over 30 minutes, when the addition was finished 75.0 g (318.6 mmol) of N-methyl-3-aminopropyltris(trimethoxy) silane was added. To the reaction was added 57.3 g (3.186 mmols) of distilled water. The reaction was stirred for 21 days and monitored by GC. During the 21 days 60.0 g (3.33 mmols) of water, 340 mL methanol, and 228.0 g (1.41 mmols) of hexamethyldisilazane were added. The reaction mixture was reduced to 125.76 g of crude oil by rotary evaporation. The crude material was distilled to give 62.6 g (169.2 mmol, 53.1%) of liquid N-methyl-3-aminopropyltris(-trimethylsiloxy)silane bp. 64' 0.125mm Hg. FTIR (neat, capillary) 2957.80, 2899.02, 2790.57, 2361.73, 1471.38, 1443.26, 1412.16, 1343.04, 1249.97, 1218.84, 1187.71, 1083.76, 833.11, 751.60, 715.03, 686.34, 658.34. NMR (CDCl₃) 2.20–2.52 (2H,t), 2.24 (3H,s), 1.13–1.66 (2H,m), 0.99 (1H,s), 0.21–0.66 (2H,m), 0.00 (27H,s).

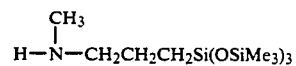

To a 500 mL 3-neck round bottom flask fitted with a magnetic stirrer, condenser, nitrogen blanket, dropping funnel, thermometer, ice-water bath was added 10.0 g (27.2 mmol) of N-methyl-3aminopropyltris (trimethyl-

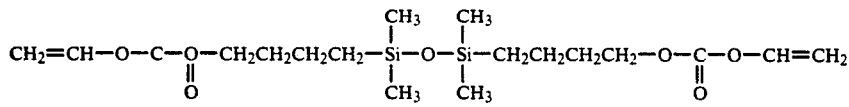

4.9 "V₂D₂₅"

To a 100 mL 1-neck round bottom microware flask fitted with a magnetic stirrer, and a drying tube was added 5.0 g (11.95 mmol) of 1,3-bis(4-vinyl butyl carbonate) tetramethyldisiloxane, 22.15 g (74.7 mmol) of octamethylcyclotetrasiloxane was added. Then 0.679 g (0.452 mmol) of trifluoromethanesulfonic acid was added to the reaction mixture. The reddish reaction mixture was stirred for 24 hours, then 0.38 g (4.52 siloxy) silane, 2.37 g (30.0 mmol) pyridine, and 200 mL ether. Next was added 3.19 g (30.0 mmol) vinyl chloroformate so that the temperature remained below 15° C. After stirring for 18 hours the reaction mixture was washed with 100 mL 2N HCl and 100 mL 2N NaOH and the organic phase was dried over magnesium sulfate. The solvent was removed on a rotary evaporator and the resulting oil was chromatographed (silica gel, methylene chloride). The product was recovered as an oil and was distilled (94°-98° C., 0.1 mm Hg) to yield 8.0 g (18.3 mmol, 67.2% yield). FTIR (neat, capillary) 2957.78, 2900.92, 1646.60, 1461.07, 1453.17, 1424.97, 1404.46, 1376.48, 1345.30, 1308.70, 1290.62, 1250.02, 1180.15, 1151.93, 1097.66, 1039.05, 952.11, 928.39, 833.42, 787.00, 753.10, 715.30. NMR (2H,t), 2.78 (3H,s), 1.20-1.70 (2H,m), 0.14-0.41 (2H,m), 0.00 (27H,s).

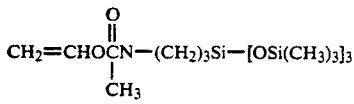

4.11 N-Vinyloxycarbonyl-N'-[tris(trimethylsiloxy)silylpropyl]piperazine

To a 500 mL 3-neck round bottom flask fitted with a mechanical stirrer, condenser, nitrogen blanket, dropping funnel, thermometer, oil bath was added 5.0 g (58.0 mmol) of piperazine and 230 mL o-xylene. The reaction mixture was heated to 125°±5° and 11.0 g (29.0 mmol) of 3-chloropropyltris(trimethylsiloxy) silane was added dropwise. The reaction was heated for 48 hours, cooled, and dried over magnesium sulfate. The solvent was removed on a rotary evaporator and the resulting oil was distilled to give the product 4.5 g (10.7 mmol, 18.4% yield). FTIR (neat, capillary) 3272.01, 2955.61, 2900.63, 2805.76, 2764.47, 2363.11, 1445.48, 1411.45, 1368.66, 1342.63, 1319.87, 1249.85, 1188.87, 1144.26, 1039.34, 833.42, 751.53, 712.61, 686.39, 656.40. NMR (CDCl₃) 3.60-3.93 (4H,m), 2.06-2.43 (6H,m), 1.66 (1H,s), 0.97-1.66 (2H,m), 0.12-0.40 (2H,m), 0.00 (27H,s).

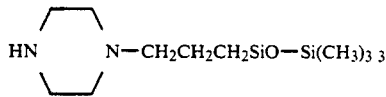

To a 250 mL 3-neck round bottom flask fitted with a magnetic stirrer, condenser, nitrogen blanket, dropping funnel, thermometer and ice-water bath was added 5.0 g (11.8 mmol) of 3-tris(trimethylsiloxy)silylpropyl piperazine, 0.98 g (12.4 mmol) pyridine and 100 mL ether. To the reaction mixture was added 1.32 g (12.4 mmol) vinyl chloroformate so that the temperature remained below 15°. After stirring for 18 hours the reaction mixture was washed with 100 mL 2N HCl, 100 mL 2N NaOH and the organic phase was dried over magnesium sulfate. The solvent was removed on a rotary evaporator and the resulting oil was chromatographed (silica gel, methylene chloride). The product was recovered as an oil 4.0 g (8.1 mmol, 68.8% yield). FTIR (neat, capillary) 2957.40, 2900.69, 2808.30, 2770.50, 1646.32, 1460.48, 1429.87, 1373.46, 1353.45, 1334.61, 1291.27, 1249.73, 1227.01, 1187.92, 1152.02, 1100.89, 1000.33, 952.03, 833.45, 752.98, 712.79, 686.52, 656.44. NMR (CDCl₃) 6.89-7.30 (1H,dd), 4.28-4.76 (2H,m), 3.30-3.60 (2H,m), 2.19-2.40 (2H,m), 1.21-1.63 (2H,m), 0.17-0.63 (2H,m), 0.00 (27H,s).

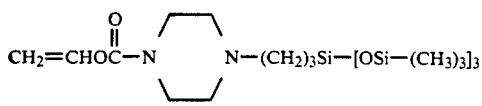

4.12 2,2-Dimethyl N,N-bis(vinyloxycarbonyl)-1,3-propandiamine C₁₁H₁₈N₂O₄

To a 250 mL 3-neck round bottom flask fitted with a magnetic stirrer, condenser, thermometer, nitrogen blanket, dropping funnel, and ice-water bath was added 15.5 g (196.0 mmol) of pyridine, 100 mL of chloroform, 10.0 g (98.0 mmol) of 2,2-dimethyl-1,3-diamino propane. After cooling to 12.5° C.±2.5° C., 20.8 g (196.0 mmol) of vinyl chloroformate was added so that the temperature was maintained. When the addition was completed, the reaction was stirred at room temperature for one hour. The organic phase was washed twice with 100 mL 2N HCl, once with distilled water, twice with 2N NaOH, once with distilled water, once with 100 mL 2N HCl, once with distilled water then was dried over magnesium sulfate. The solvent was removed on a rotary evaporator and the resulting solid was chromatographed (silica gel, ethyl acetate) to afford a white solid (mp 92°-98° C.), 14.4 g (59.5 mmol, 60.7%). FTIR 3356.25, 3330.18, 3101.77, 3091.71, 3047.38, 2967.99, 2962.39, 2932.08, 2875.70, 1733.54, 1725.58, 1710.82, 1676.99, 1649.18, 1527.92, 1473.90, 1458.90, 1440.71, 1394.41, 1371.29, 1360.72, 1299.03, 1257.64, 1244.48, 1201.55, 1157.95, 1106.46, 1062.40, 1025.93, 998.01, 979.97, 961.45, 951.57, 876.82, 866.36, 774.00, 720.42, 671.33. NMR (CDCl₃) 6.93-7.27 (2H,m), 5.46-5.93 (2H,s), 4.428-4.86 (4H,m), 2.83-3.10 (4H,d), 0.90 (6H,s).

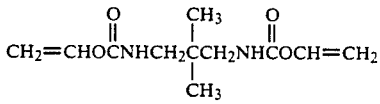

4.13 N-(2-ethyl vinyl carbonate)-3-aminopropyltris(trimethylsiloxy) silane

To a 250 mL 3-neck round bottom flask fitted with a mechanical stirrer, condenser, nitrogen blanket, dropping funnel, oil bath, thermometer was added 104.3 g (1021.0 mmol) 2,2-dimethyl-1,3-diaminopropane, 29.3 g (79.0 mmol) of 3-chloropropyltris (trimethylsiloxy) silane. The reaction was heated at 120° C. for 3 hours and stirred to room temperature for 24 hours. The reaction mixture was washed with 100 mL 2N NaOH then the organics were dried over magnesium sulfate. The solvent was removed on a rotary evaporator and the resulting oil distilled to give 23.8 g (54.3 mmol, 68.6% yield) bp 100° C. FTIR (neat, capillary) 2955.72, 2807.97, 2361.44, 1614.95, 1463.73, 1409.81, 1362.71, 1249.98, 1185.85, 1039.44, 833.64, 753.04, 714.78, 686.41, 657.85. NMR (CDCl₃) 2.25-2.56 (6H,m), 1.19-1.63 (2H,m), 1.06 (3H,s), 0.78 (6H,s), 0.07-0.45 (2H,m), 0.00 (27H,s).

To a 250 mL 3-neck round bottom flask fitted with a magnetic stirrer, condenser, nitrogen blanket, dropping funnel, ice-water bath, thermometer was added 6.3 g (15.8 mmol) N-(2-hydroxyethyl)-3-aminopropyltris(trimethylsiloxy) silane, 1.37 g (17.4 mmol) of pyridine, 100 mL ether. To the reaction mixture was added 1.68 g (15.8 mmol) of vinyl chrloroformate so that the temperature remained to below 5° C.

After stirring to room temperature for 24 hours the reaction mixture was washed with 100 mL 2N HCl then 100 mL 2N NaOH then the organics were dried over magnesium sulfate. The solvent was removed on a rotary evaporator and the resulting oil, 4.3 g, chromatographed (silica gel, ethyl acetate 20% methylene chloride 80%). The oil recovered weighed 2.99 g (6.4 mmol, 25.4% yield). FTIR (neat, capillary) 2957.62, 2899.00, 1720.60, 1702.33, 1648.16 1470.55, 1420.23, 1373.91, 1291.12, 1249.88, 1196.62, 1152.74, 1039.27, 951.52, 833.44, 753.18, 715.26, 686.53, 658.78. NMR (CDCl₃) 6.85–7.20 (1H,dd), 4.20–4.69 (2H,m), 3.36–3.71 (2H,bd), 3.00–3.36 (4H,m), 1.00–1.65 (2H,m), 0.09–0.40 (2H,m), 0.00 (27H,s).

4.14 3-[Tris(trimethylsiloxy)silyl]propylaminoethyl vinyl carbonate

To a 500 mL 3-neck round bottom flask fitted with a magnetic stirrer, condenser, nitrogen blanket, oil bath and thermometer was added 100 mL ethanolamine, 20.0 g (53.5 mmol) of 3-chloropropyltris (trimethylsiloxy) silane. The reaction was heated at 120° C. for 4 hours then at 140° C. for 1 hour. The reaction was cooled then diluted with 400 mL distilled water then extracted twice with 100 mL ether. The combined organics were dried over magnesium sulfate. The solvent was removed on a rotary evaporator and the resulting oil, 23.0 g, chromatographed (silica gel, gradient from 98.75% $CH_2Cl_2$, 1.25% EtOAc to 100% MeOH) to give 6.6 g (16.6 mmol, 31.1%) FTIR (neat, capillary) 2957.55, 2898.62, 2834.28, 1453.19, 1411.46, 1249.92, 1191.11, 1039.00, 833.12, 751.49, 714.58, 686.18, 657.92. NMR (CDCl₃) 3.09–3.68 (4H,m), 2.25–2.43 (4H,m), 1.17–1.71 (2H,m), 0.07–0.47 (2H,m), 0.00 (27H,s).

To a 250 mL 3-neck round bottom flask fitted with a magnetic stirrer, condenser, nitrogen blanket, dropping funnel, ice-water bath and thermometer was added 6.3 g (15.8 mmol) N-(2-hydroxyethyl)-3-aminopropyltris(-trimethylsiloxy) silane, 1.37 g (17.4 mmol) of pyridine and 100 mL ether. To the reaction mixture was added 1.68 g (15.8 mmol) of vinyl chloroformate so that the temperature remained below 5° C. After stirring at room temperature for 24 hours the reaction mixture was washed with 100 mL 2N HCl, 100 mL 2N NaOH and the organic phase was dried over magnesium sulfate. The solvent was removed on a rotary evaporator and the resulting oil, 4.3 g, chromatographed (silica gel, ethyl acetate 20% methylene chloride 80%). The oil recovered weighed 2.99 g (6.4 mmol, 25.4% yield). FTIR (neat, capillary) 2957.62, 2899.00, 1720.60, 1702.33, 1648.16, 1470.55, 1420.23, 1373.91, 1291.12, 1249.88, 1196.62, 1152.74, 1039.27, 951.52, 833.44, 753.18, 715.26, 686.53, 658.78. NMR (CDCl₃) 6.85–7.20 (1H,dd), 4.20–4.69 (2H,m), 3.36–3.71 (2H,bd), 3.00–3.36 (4H,m), 1.00–1.65 (2H,m), 0.09–0.40 (2H,m), 0.00 (27H,s).

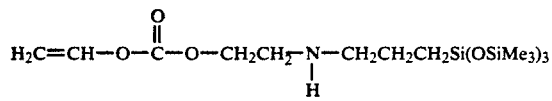

PART V—CYCLOALKYL AND CYCLOARYL CONTAINING MONOMERS 5.0 4-s-Butylphenyl Vinyl Carbonate $C_{13}H_{16}O_3$ To a 250 mL 1-neck round bottom flask fitted with a magnetic stirrer, dropping funnel, ice-bath was added 10.0 g (66.6 mmol) of 4-s-butylphenol, 5.8 g (73.3 mmol) of pyridine and 100 mL of chloroform. To the stirred solution 7.08 g (66.6 mmol) of vinyl chloroformate was added over 5 minutes and the reaction mixture stirred for 30 minutes until pyridine hydrogen chloride precipitated. The organic phase was washed twice with 100 mL of 2NHCl, dried over magnesium sulfate and the solvent removed on a rotary evaporator to give an oil. Following chromatography (silica gel, toluene), 9.6 g (43.6 mmol, 65.4%) of colorless oil was obtained. FTIR (neat, capillary) 2962.40, 2929.59, 2875.00, 1770.07, 1650.57, 1507.20, 1456.70, 1378.92, 1298.73, 1218.82, 1201.06, 1172.56, 1128.61, 1052.11, 1016.02, 997.93, 941.57, 913.17, 874.55, 835.99, 771.64, 730.98, 707.91, 696.57. NMR (CDCl₃) 7.08 (4H,S), 6.90–7.23 (1H,m), 4.50–5.10 (2H,m), 2.31–2.78 (1H,m), 1.33–1.81 (2H,m), 1.16–1.23 (2H,d), 0.68–1.00 (3H,m).

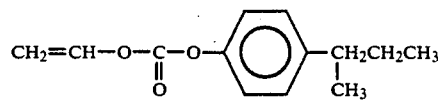

5.1 4-t-Butylphenyl Vinyl Carbamate $C_{13}H_{17}NO_2$

To a 250 mL 3-neck round bottom flask fitted with a magnetic stirrer, condenser, nitrogen blanket, thermometer, dropping funnel, ice water bath was added 7.1 g (80.0 mmol) of pyridine, 87.5 mL of chloroform, 12.0 g (80.0 mmol) of 4-t-butylaniline. After cooling to 12.5° C., 8.6 g (80.0 mmol) of vinyl chloroformate was added so that the temperature was maintained. When the addition is completed, reaction was stirred at room temperature for 3 hours. The organic phase was washed twice with 100 mL 2N HCl, once with distilled water, twice with 2N NaOH, once with distilled water, once with 100 mL 2NHCl, once with distilled water, and dried over magnesium sulfate. The solvent was removed on a rotary evaporator and the resulting solid was chromatographed (silica gel, CHCl₃) to give a white solid (mp 83°–85° C.) 14.0 g (65.1 mmol, 81.4%). FTIR (KBr) 3317.67, 3248.14, 2960.58, 2903.46, 2868.29, 1718.64, 1649.04, 1615.15, 1600.07, 1543.48, 1476.36, 1460.81, 1412.07, 1363.76, 1324.04, 1301.85, 1270.05, 1244.76, 1152.47, 1123.96, 1113.56, 1064.50, 1016.24, 954.13, 858.83, 828.57, 744.72, 704.65, 681.65. NMR (CDCl₃) 7.27 (4H,S), 7.03–7.40 (1H,m), 6.64–6.82 (1H,S), 4.37–4.90 (2H,m), 1.27 (9H,S).

5.2 4-t-Butylcyclohexyl Vinyl Carbonate

To a 250 mL 3-neck round bottom flask fitted with a magnetic stirrer, condenser, thermometer, ice water bath, dropping funnel, was added 10.0 g (64.0 mmol) of 4-t-butylcyclohexanol, 5.6 g (70.3 mmol) of pyridine and 100 mL of chloroform. The reaction mixture was cooled to less than 10° C. and 6.8 g (64.0 mmol) of vinyl chloroformate was added so that the temperature remained below 15° C. The reaction mixture was stirred at room temperature for 20 hours, then washed with 100 mL 2N HCl, 100 mL distilled water and dried over magnesium sulfate. The solvent was removed on a rotary evaporator and the resulting oil chromatographed (silica gel, methylene chloride) to afford 7.3 g (32.28 mmol, 50.4%) of an oil. FTIR (neat, capillary) 2949.85, 2867.24, 1753.81, 1650.71, 1478.96, 1468.77, 1452.57, 1393.73, 1385.90, 1361.15, 1325.03, 1296.75, 1246.94, 1193.82, 1178.29, 1155.10, 1118.52, 1106.53, 1083.32, 1041.01, 1016.58, 1005.94, 946.14, 923.71, 902.63, 867.23, 843.74, 804.43, 783.98, 758.83, 696.74, 668.14. NMR (CDCl₃) δ 6.86–7.22 (1H,m), 4.37–4.97 (2H,m), 1.00–2.30 (10H,m), 0.85 (9H,S).

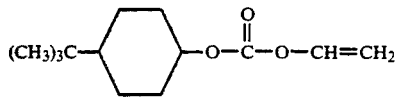

PART VI—ADDITIONAL MONOMER SYNTHESIS

6.0 1-Adamantane vinyl carbonate

To a 500 mL 3-neck round bottom flask fitted with a mechanical stirrer, condenser, nitrogen blanket, dropping funnel, ice-saltwater bath and thermometer was added 17.6 g (116.0 mmol) of 1-adamantanol, 9.3 g (117.0 mmol) of pyridine and 200 mL chloroform. To the reaction misture was added 12.5 g (117.0 mmol) of vinyl chloroformate so that the temperature remained below 10 degrees centigrade. After stirring at room temperature for 18 hours the reaction mixture was washed with 100 mL 2N HCl and 100 mL 2N NaOH and the organic phase was dried over magnesium sulfate. The solvent was removed on a rotary evaporator and the resulting white solid chromatographed (silica gel, chloroform). The white solid recovered 19.3 g (86.4 mmol, 74.5% yield) melting point 35–37 degrees centigrade. FTIR (KBr) 3430.92, 2914.51, 2855.03, 1756.33, 1651.33, 1458.19, 1321.61, 1312.23, 1296.45, 1246.83, 1160.25, 1103.75, 1082.53, 1041.68, 964.82, 892.90, 784.44. NMR (CDCl₃) 6.81–7.20 (1H,dd), 4.33–4.96 (2H,m), 1.50–2.40 (15H,m)

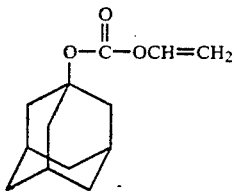

6.1 1-Adamantanemethyl Vinyl Carbonate

To a 500 mL 3-neck round bottom flask fitted with a mechanical stirrer, condenser, nitrogen blanket, dropping funnel, ice-saltwater bath and thermometer was added 10.0 g (60.0 mmol) of 1-adamantanmethanol, 4.8 g (60.0 mmol) of pyridine and 150 mL chloroform. To the reaction mixture was added 6.4 g (60.0 mmol) of vinyl chloroformate so that the temperature remained below 10° C. After stirring at room temperature for 18 hours the reaction mixture was washed with 100 mL 2N HCl and 100 mL 2N NaOH and the organic phase was dried over magnesium sulfate. The solvent was removed on a rotary evaporator and the resulting solid chromatographed (silica gel, chloroform). The white solid recovered totaled 12.0 g (50.8 mmol, 84.5% yield), melting point 44°–45° C. FTIR (KBr) 3423.04, 2906.49, 2580.27, 1759.74, 1649.15, 1391.84, 1322.44, 1260.77, 1231.42, 1190.53, 1147.22, 1087.78, 982.05, 951.64, 938.71, 889.75. NMR (CDCl₃) 6.89–7.27 (1H,dd), 4.40–5.05 (2H,m), 3.75 (2H,s), 1.43–2.13 (15H,m)

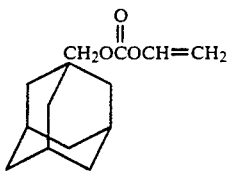

6.2 1-Adamantane Vinyl Carbonate)

To a 500 mL 3-neck round bottom flask fitted with a mechanical stirrer, condenser, nitrogen blanket, dropping funnel, ice-saltwater bath, thermometer was added 5.0 g (27.7 mmol) of 1-adamanthanethanol, 2.2 g (27.7 mmol) of pyridine and 150 mL chloroform. To the reaction mixture was added 2.95 g (28.0 mmol) of vinyl chloroformate so that the temperature remained below 10 degrees centigrade. After stirring at room temperature for 18 hours the reaction mixture was washed with 100 mL 2N HCl and 100 mL 2N NaOH and the organic phase dried over magnesium sulfate. The solvent was removed on a rotary evaporator and the resulting oil chromatographed (silica gel, chloroform). The oil recovered totaled 27.6 g (10.8 mmol, 38.5% yield). FTIR (neat, capillary) 2898.57, 2846.95, 1756.14, 1648.61, 1450.70, 1398.71, 1312.71, 1296.74, 1240.05, 1155.26, 1106.22, 1097.88, 1090.63, 975.27, 944.26, 933.77, 923.00, 900.75, 867.0, 782.34. NMR (CDCl₃) 6.86–7.20 (1H,dd), 4.38–4.92 (2H,m), 4.072–4.37 (2H,t), 1.33–2.18 (17H,m).

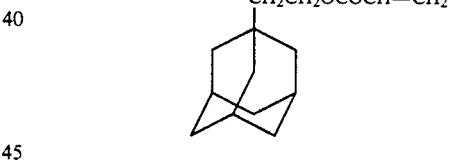

6.3 1-Adamantane Vinyl Carbamate

To a 500 mL 3-neck round bottom flask fitted with a mechanical stirrer, condenser, nitrogen blanket, dropping funnel, ice-saltwater bath and thermometer was added 10.0 g (66.0 mmol) of 1-adamantaneamine, 5.5 g (70.0 mmol) of pyridine and 150 mL chloroform. To the reaction mixture was added 7.4 g (70.0 mmol) of vinyl chloroformate so that the temperature remained below 10° C. After stirring at room temperature for 18 hours the reaction mixture was washed with 100 mL 2N HCl and 100 mL 2N NaOH and the organic phase was dried over magnesium sulfate. The solvent was removed on a rotary evaporator and the resulting solid was chromatographed (silica gel, chloroform). The tan solid totaled 5.2 g (23.5 mmol, 35.6% yield). FTIR (KBr) 3435.97, 3341.23, 2919.85, 2906.82, 2852.95, 1738.71, 1718.23, 1648.31, 1522.76, 1362.95, 1347.11, 1296.03, 1280.55, 1229.09, 1188.08, 1173.23, 1131.46, 1054.34, 1044.05, 952.14, 849.30. NMR (CDCl₃) 6.94–7.33 (1H,dd), 4.25–4.88 (3H,m), 1.56–2.26 (15H,m).

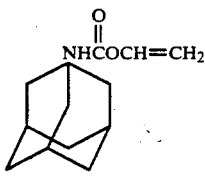

6.4 N-(2-adamantyl)-0-2-Vinyloxycarbonylaminoethyl Carbamate

To a 250 mL 3-neck round bottom flask that was fitted with a magnetic stirrer, condenser, nitrogen blanket, was added 6.33 g (41.8 mmol) of 2-adamantamine, 20.7 g (41.8 mmol) of 20% phosgene in toluene and 90 mL of dry toluene. By means of a heating mantle the reaction was refluxed for eight hours, then allowed to cool to room temperature over night. To the reaction mixture was added 5.0 g (38.0 mmol) of 2-hydroxyethyl vinyl carbamate in 100 mL of dry toluene. The reaction mixture was refluxed for eight hours then cooled to room temperature and the product was filtered and dried to give 5.4 g (17.5 mmol, 46.1% yield). FTIR (Kbr) 3320.53, 2911.77, 2854.81, 2708.48, 2622.82, 2587.66, 2530.60, 2062.48, 1710.68, 1648.47, 1625.62, 1604.50, 1594.43, 1514.68, 1476.34, 1453.03, 1403.83, 1363.71, 1348.91, 1323.96, 1311.36, 1295.64, 1250.12, 1185.17, 1111.58, 1056.19, 1012.80, 974.49, 949.05, 913.42, 863.76, 810.32, 769.55, 730.73, 694.94, 649.43. NMR (CDCl$_3$) 8.54-7.54 (2H,bs), 7.33-6.96 (1H,q), 4.85-4.26 (2H,m), 3.79-3.20 (4H,m), 2.33-1.33 (15H,m).

6.5 N,N-dimethyl vinyl carbamate

To a 100 mL 3-neck round bottom flask fitted with a mechanical stirrer, condenser, nitrogen blanket, thermometer, fritted gas delivery tube, methanol-dry icebath was added 23.8 g (223.4 mmol) of vinyl chloroformate, 650 mL of ether. When the reaction mixture was at −65° C. a stream of dimethylamine was added for 30 minutes. By gas chromatography the vinyl chloroformate was consumed. The reaction was stirred to room temperature over night. The organics were washed with 500 mL distilled water then dried over magnesium sulfate. The solvent was removed on a rotary evaporator and the resulting oil (20.3 g) distilled to give 9.3 g (80.8 mmol, 36.2%). FTIR (neat, capillary) 3091.32, 2932.23, 1712.80, 1645.80, 1520.23, 1488.98, 1445.42, 1396.96, 1370.59, 1291.08, 1275.79, 1165.47, 1144.50, 1082.71, 1042.05, 951.61, 923.80, 859.37, 835.80, 758.66, 699.77, 681.97. NMR (CDCl$_3$) 7.02-7.33 (1H,q), 4.25-4.79 (2H,m), 2.92 (6H,s).

6.6 N,N-diethyl vinyl carbamate

To a 250 mL 3-neck round bottom flask fitted with a magnetic stirrer, condenser, nitrogen blanket, dropping funnel was added 3.2 g (26.25 mmol) of potassium t-butoxide, 50 mL anhydrous tetrahydrofuran. After the solid was dissolved 5.6 g (25.0 mmol) of N,N-diethyl 2-bromoethyl carbamate was added and the reaction stirred for 30 minutes. To the reaction was added 100 mL distilled water then the solvent was removed on the rotary evaporator. The residue was taken up in ether and filtered then distilled to give an oil 2.57 g (17.9 mmol, 71.8% yield). FTIR (neat, capillary) 2976.21, 2936.84, 2878.45, 1710.65, 1645.97, 1522.34, 1474.22, 1458.46, 1422.71, 1379.10, 1366.22, 1350.76, 1316.26, 1290.78, 1269.99, 1224.27, 1160.58, 1143.97, 1097.99, 1085.35, 1077.10, 1059.36, 987.36, 951.76, 858.41, 820.83, 781.32, 760.94, 699.54. NMR (CDCl$_3$) 7.07-7.39 (1H,q), 4.31-4.89 (2H,m), 3.12-3.46 (4H,q), 1.05-1.31 (6H,t).

ADDITIONAL INTERMEDIATES

2-Bromoethyl vinyl carbonate

To a 1 L 4-neck round bottom flask fitted with a mechanical stirrer, thermometer, condenser, dropping funnel and nitrogen blanket was added 31.2 g (250 mmol) of 2-bromoethanol, 21.4 g (270 mmol) of pyridine and 400 mL of ether. The reaction was cooled with an ice-water bath to less than 10° C. then 28.8 g (270 mmol) of vinyl chloroformate was added so that the temperature remained below 10° C. The reaction was stirred to room temperature for 27 hours. Then the organics were washed twice with 2N HCl, twice with 2N NaOH, then dried over magnesium sulfate. The solvent was removed on a rotary evaporator and the resulting oil was passed through a short silica gel column, to remove most of the color, to give 38.4 g (197 mmol, 78.8% yield). FTIR (neat, capillary) 3672.76, 3469.03, 3096.75, 2972.97, 2155.40, 2057.14, 1754.37, 1648.44, 1563.96, 1455.87, 1443.36, 1427.17, 1388.17, 1299.17, 1285.60, 1244.29, 1221.29, 1152.23, 1095.86, 1049.38, 988.10, 940.93, 897.08, 875.78, 828.81, 778.74, 738.01, 694.54, 663.28. NMR (CDCl$_3$) 6.85-7.23 (1H,q), 4.40-5.10 (4H,m), 3.42-3.59 (2H,t).

N,N-diethyl-2-bromoethyl carbamate

To a 500 mL 3-neck round bottom flask fitted with a mechanical stirrer, condenser, nitrogen blanket, thermometer, dropping funnel was added 19.3 g (263.8 mmol) of diethylamine and 250 mL of dry toluene. To the reaction mixture was added 24.7 g (131.9 mmol) of 2-bromoethyl chloroformate. An exotherm to 40° C. was noted along with the formation of a precipitate. After 1 hour at 70° C. the organics were washed with 2N HCl then dried over magnesium sulfate. The solvent was removed on the rotary evaporator and the resulting oil distilled to give 6.5 g (29.0 mmol, 22% yield). FTIR (neat, capillary) 2973.85, 2934.58, 2875.90, 1692.95, 1478.36, 1458.21, 1422.49, 1379.09, 1365.61, 1350.53, 1314.77, 1267.60, 1224.49, 1164.67, 1093.11, 1075.29, 1003.67, 962.05, 948.43, 766.15, 647.29. NMR (CDCl$_3$) 4.23-4.49 (2H,t), 3.49-3.66 (2H,t), 3.10-3.52 (4H,q), 1.04-1.33 (6H,t).

PREFERRED CROSSLINKERS

PART VII—SYNTHESIS OF SIMPLE CROSSLINKERS

7.0 Propargyl Vinyl Carbonate C$_6$H$_6$O$_3$

To a 500 mL 3-neck round bottom flask fitted with a magnetic stirrer, condenser, nitrogen blanket, thermometer, dropping funnel, and cooled within ice water bath was added 20.0 g (356.8 mmol) of propargyl alcohol, 31.0 g (356.8 mmol) of pyridine, 100 mL of acetonitrile and 250 mL of ether. After cooling to 5° C., 38.0 g (356.8 mmol) of vinyl chloroformate was added so that the temperature stayed below 10° C. The organic phase was washed with 400 mL 2NHCl, 200 mL 2N NaOH and dried with magnesium sulfate. The solvent was removed on a rotary evaporator and the resulting oil was passed through an 8 gram silica gel pad to afford a colorless oil 36.0 g (285.5 mmol, 80%). FTIR (neat, capillary) 3297.26, 1757.06, 1652.22, 1439.81, 1386.65, 1299.36, 1152.11, 1087.82, 1016.04, 964.84, 941.81, 915.98, 879.03, 779.08, 676.61, 663.07, 656.20. NMR (CDCl$_3$) 6.83-7.17 (1H,m), 4.43-5.05 (2H,m), 4.63-4.87 (2H,m), 2.46-2.60 (1H,m).

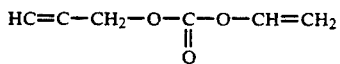

PART VIII—OXYALKYLENE BRIDGED CROSSLINKERS

8.0 1,2-bis-(Vinyloxycarbonyloxy)ethane

To a 100 mL 3-neck round bottom microware flask fitted with a magnetic stirrer, condenser, N$_2$ blanket, and dropping funnel was added 5.0 g (81.6 mmol) of ethylene glycol, 12.8 g (163.0 mmol) of pyridine and 50 mL of chloroform. To the reaction mixture, 17.38 g (163.2 mmol) of vinyl chloroformate was added over 5 minutes. The black reaction mixture was stirred at room temperature for 72 hours. The reaction mixture was washed once with 100 mL 2N HCl, once with 100 mL 2N NaOH and then dried over magnesium sulfate. The solvent was removed on a rotary evaporator and the resulting oil chromatographed (silica gel, chloroform). The product was distilled (110° C., 5 Torr) to afford 6.5 g (32.2 mmol, 39.4%) of a colorless oil. FTIR (neat, capillary) 1752.03, 1648.58, 1455.73, 1445.68, 1406.42, 1386.28, 1373.53, 1345.23, 1301.17, 1268.47, 1221.46, 1152.52, 1080.66, 1028.57, 1007.91, 941.86, 903.05, 866.96, 777.05, 696.37. NMR (CDCl$_3$)δ 6.85-7.18 (2H,m), 4.52-5.04 (4H,m), 4.40 (4H,S).

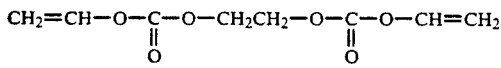

8.1 α,ω-bis-(Vinyloxycarbonyl)triethyleneglycol C$_{12}$H$_{18}$O$_8$

To a 500 mL 3-neck round bottom flask fitted with a magnetic stirrer, condenser, thermometer, nitrogen blanket, and dropping funnel was added 10.0 g (66.6 mmol) of triethyleneglycol, 5.79 g (73.3 mmol) of pyridine and 100 mL of chloroform. Next, was added 7.80 g (73.3 mmol) of vinyl chloroformate, an exotherm was noted and the reaction mixture was stirred at room temperature for 18 hours. The organic phase was washed twice with 100 mL 2N HCl, twice with 100 mL 2N NaOH and dried with magnesium sulfate. The solvent was removed on a rotary evaporator to give an oil that was chromatographed (silica gel, CHCl$_3$) to afford an oil 2.6 g (8.9 mmol, 13.5%). FTIR (neat, capillary) 2959.95, 2877.99, 1752.00, 1648.22, 1453.36, 1388.35, 1368.46, 1355.89, 1337.65, 1298.80, 1234.17, 1152.82, 1082.40, 1023.62, 943.56, 902.67, 869.75, 779.08, 697.03. NMR (CDCl$_3$) 6.98-7.63 (2H,m), 4.40-5.03 (4H,m), 4.20-4.40 (4H,m), 3.60-3.80 (48,m).

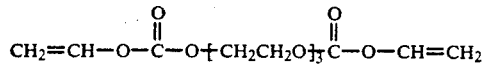

8.2 α,ω-bis-(Vinyloxycarbonyl)polyethylene Glycol C$_{26}$H$_{46}$O$_{15}$

To a 500 mL 3-neck round bottom flask fitted with a magnetic stirrer, condenser, nitrogen blanket, thermometer, and dropping funnel was added 10.0 g (16.6 mmol) of poly(ethyleneglycol), 3.2 g (36.5 mmol) of pyridine and 200 mL of chloroform. Next, 3.9 g (36.5 mmol) of vinyl chloroformate in 5 mL chloroform was added. A slight exotherm to 30° C. was noted. The reaction was stirred at room temperature for 48 hours and the organic phase washed twice with 100 mL 2N HCl, twice with 100 mL 2NaOH, and dried over magnesium sulfate. The solvent was removed on a rotary evaporator and the resulting oil was chromatographed (silica gel, CHCl$_3$) to afford 1.3 g (2.17 mmol, 13.0%) of colorless oil. FTIR (neat, capillary) 2867.87, 1756.21, 1648.17, 1455.18, 1388.46, 1350.26, 1298.44, 1247.57, 1083.45, 1026.37, 944.30, 871.74, 781.69. NMR (CDCl$_3$) 6.85-7.17 (2H,m), 4.34-5.00 (4H,m), 3.60-4.35 (40H,m).

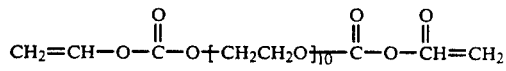

8.3 α,ω-bis(Vinyloxycarbonyl) Polypropylene Glycol (mw approx. 1000)

To a 500 mL 3-neck round bottom flask fitted with a mechanical stirrer, condenser, nitrogen blanket, dropping funnel, ice-saltwater bath and thermometer was added 20.0 g (47.0 mmol) polypropylene glycol (mw 1000) 7.6 g (96.0 mmol) of pyridine and 200 mL chloroform. To the reaction mixture was added 10.2 g (96.0 mmol) of vinyl chloroformate so that the temperature remained below 10 degrees centigrade. After stirring at room temperature for 48 hours the reaction mixture was washed with 100 mL 2N HCl, 100 mL 2N NaOH and the organic phase dried over magnesium sulfate. The solvent was removed on a rotary evaporator and the resulting oil chromatographed (short column silica gel, chlorform). The oil recovered weighed 14.6 g (25.9 mmol, 55.0% yield). FTIR (neat, capillary) 3096.15, 2973.01, 2934.02, 2870.93, 2335.49; 1754.56, 1648.30, 1568.82, 1453.53, 1375.64, 1349.76, 1296.84, 1249.99, 1152.61, 1083.39, 1051.95, 1018.85, 944.06, 923.43, 908.46, 868.85, 783.82, 697.48, 668.50. NMR (CDCl$_3$) 6.86-7.23 (2H,dd), 4.61-5.06 (4H,m), 3.33-3.76 (21H,m), 1.03-1.43 (21H,m).

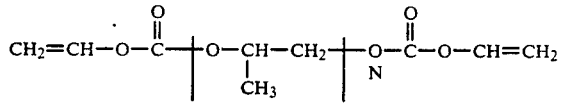

Where N is an average value that gives the polypropylene glycol moiety an average molecular weight of about 1000.

8.4 α,ω-Bis(Vinyloxycarbonylpolyethylene Glycol mw approx. 1000

To a 500 mL 3-neck round bottom flask fitted with a mechanical stirrer, condenser, nitrogen blanket, dropping funnel, ice-saltwater bath and thermometer was added 20.0 g (20.0 mmol) polyethylene glycol (mw 1000), 3.5 g (44.0 mmol) of pyridine, 200 mL chloroform. To the reaction mixture was added 4.7 g (44.0 mmol) of vinyl chloroformate so that the temperature remained below 10° C. After stirring at room temperature for 48 hours the reaction mixture was washed with 100 mL 2N HCl and 100 mL 2N NaOH and the organic phase was dried over magnesium sulfate. The solvent was removed on a rotary evaporator and the resulting low melting solid weighed 18.0 g (16.0 mmol, 79.9% yield). FTIR (neat, capillary) 3477.73, 2868.36, 2360.96, 1959.64, 1758.88, 1725.44, 1648.24, 1465.99, 1453.61, 1388.65, 1358.03, 1342.58, 1298.64, 1255.02, 1142.06, 1100.49, 1060.10, 944.47, 872.48, 841.08, 782.12, 756.09, 730.85, 699.44. NMR (CDCl$_3$) 6.83–7.20 (2H,dd), 4.40–4.96 (4H,m), 3.58 (88H,s).

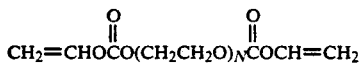

Where N is an average value that gives the polyethylene glycol moiety an average molecular weight of about 1000.

PART IX—SYNTHESIS OF BRANCHED ALKYL BRIDGED CROSSLINKERS

9.0 2,2-Dimethyl-1,3-bis-(Vinyloxycarbonyloxy)propane

To a 500 mL 3-neck round bottom flask fitted with a magnetic stirrer, condenser, thermometer, ice-water bath, and dropping funnel was added 20.0 g (192.0 mmol) of 2,2-dimethyl-1,3-propaneidiol, 16.7 g (211.2 mmol) of pyridine and 200 mL of chloroform. To the reaction mixture was added 20.45 g (192.0 mmol) of vinyl chloroformate was added over 20 minutes. After 1 hour, the reaction was allowed to warm to room temperature for 20 hours. The organic phase was washed twice with 100 mL 2N HCl, twice with 100 mL 2N NaOH and then dried over magnesium sulfate. The solvent was removed on a rotary evaporator to afford an oil. Following chromatography (silica gel, 80% heptane, 20% methylene chloride) 6.4 g (26.2 mmol, 13.6%) of colorless oil was obtained. FTIR (neat, capillary) 2970.57, 1754.14, 1650.67, 1566.46, 1540.34, 1476.77, 1406.71, 1386.46, 1375.68, 1299.22, 1227.23, 1152.73, 1085.68, 1054.54, 1020.91, 961.81, 941.38, 871.66, 779.08, 696.42. NMR (CDCl$_3$) δ 6.80–7.18 (1H,m), 4.45–4.98 (2H,m), 3.98 (4H,S), 1.04 (6H,S).

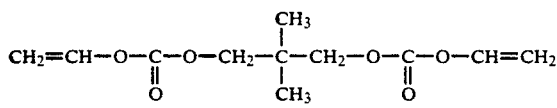

9.1 N,O-bis-(Vinyloxycarbonyl)ethanolamine C$_8$H$_{11}$O$_5$

To a 250 mL 3-neck round bottom flask fitted with a magnetic stirrer, condenser, thermometer, nitrogen blanket, dropping funnel and an ice-water bath was added 27.2 g (344.0 mmol) of pyridine, 10.0 g (164.0 mmol) of aminoethanol and 100 mL of ether. Next, 36.7 g (344.0 mmol) of vinyl chloroformate was added so that the temperature remained below 15° C. The reaction was stirred at room temperature for 72 hours and 50 mL acetonitrile and 5.0 g (50.0 mmol) of vinyl chloroformate were added. The mixture was stirred 24 hours and the organic phase washed thrice with 100 mL 2N HCl, twice with 100 mL distilled water, thrice with 100 mL 2N NaOH, twice with 100 mL distilled water, once with 100 mL 2N HCl, once with 100 mL distilled water and then dried with magnesium sulfate. The solvent was removed on a rotary evaporator to give a solid which was chromatographed (silica gel, CHCl$_3$) recrystallized (toluene: heptane, 2:8) to afford a white solid (mp 45°–46° C.), 9.4 g (46.7 mmol, 27.2%). FTIR (KBr) 3507.66, 3318.44, 3124.82, 3047.20, 2998.82, 2967.94, 2952.25, 2849.60, 2754.60, 1761.20, 1734.02, 1707.59, 1679.14, 1650.91, 1540.99, 1465.42, 1433.12, 1399.05, 1383.81, 1368.76, 1306.65, 1275.59, 1173.28, 1156.81, 1116.49, 1088.57, 1033.54, 1008.11, 964.70, 948.83, 928.54, 902.88, 887.36, 877.39, 850.91, 782.45, 699.45, 699.43. NMR (CDCl$_3$) 6.83–7.32 (1H,m), 5.06–5.43 (1H,S), 4.37–5.06 (2H,m), 4.27–4.36 (2H,m), 3.30–3.70 (2H,m).

9.2 2,2-Dimethyl-N,N-bis(vinyloxycarbonyl)-1,3-propanediamine C$_{11}$H$_{18}$N$_2$O$_4$ To a 250 mL 3-neck round bottom flask fitted with a magnetic stirrer, condenser, thermometer, nitrogen blanket, dropping funnel, and ice-water bath was added 15.5 g (196.0 mmol) of pyridine, 100 mL of chloroform and 10.0 g (98.0 mmol) of 2,2-dimethyl-1,3-diaminopropane. After cooling to 12.5° C.±2.5° C., 20.8 g (196.0 mmol) of vinyl chloroformate was added so that the temperature was maintained. When the addition was complete, the reaction was stirred at room temperature one hour. The organic phase was washed twice with 100 mL 2N HCl, once with distilled water, twice with 2N NaOH, once with distilled water, once with 100 mL 2N HCl, once with distilled water and then dried over magnesium sulfate. The solvent was removed on a rotary evaporator and the resulting solid was chromatographed (silica gel, ethyl acetate) to afford a white solid (mp 92°–98° C.), 14.4 g (59.5 mmol, 60.7%). FTIR 3356.25, 3330.18, 3101.77, 3091.71, 3047.38, 2967.99, 2962.39, 2932.08, 2875.70, 1733.54, 1725.58, 1710.82, 1676.99, 1649.18, 1527.92, 1473.90, 1458.90, 1440.71, 1394.41, 1371.29, 1360.72, 1299.03, 1257.64, 1244.48, 1201.55, 1157.95, 1106.46, 1062.40, 1025.93, 998.01, 979.97, 961.45, 951.57, 876.82, 866.36, 774.00, 720.42, 671.33. NMR (CDCl$_3$) 6.93–7.27 (2H,m), 5.46–5.93 (2H,S), 4.428–4.86 (4H,m), 2.83–3.10 (4H,d), 0.90 (6H,S).

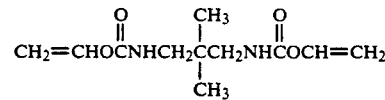

9.3 1,6-divinylhexyldicarbamate

To a 500 mL 3-neck round bottom flask fitted with a magnetic stirrer, condenser, nitrogen blanket, dropping funnel, thermometer was added 5.0 g (43 mmol) of 1,6 diaminohexane, 7.12 g (90 mmol) of pyridine, 100 mL anhydrous acetonitrile, 100 mL ether. After the starting material was dissolved 9.26 g (87 mmol) of vinyl chloroformate was added over 20 minutes an exotherm was noted, and a precipitate formed over 18 hours. The solvent was removed on a rotary evaporator and the residue was dissolved in methylene chloride, washed with 2N NaOH, thrice with distilled water then dried with magnesium sulfate. The solid was coated on silica gel and chromatographed (97% CH$_2$Cl$_2$, 3% ETOAc) to give a solid that was dissolved in methylene chloride and slowly added to stirred heptane. The solid recovered was dried to give 5.7 g (22.2 mmol, 51.7% yield) melting point 94°-98° C. FTIR 3333.74, 3086.01, 3032.62, 2947.83, 2886.20, 2857.98, 1713.28, 1682.02, 1648.85, 1528.09, 1476.87, 1465.92, 1339.48, 1294.01, 1259.77, 1224.55, 1156.32, 1051.88, 1001.10, 954.5, 875.05, 866.57. NMR (CDCl₃) 7.00-7.34 (2H,q) 4.62-5.13 (2H,bs), 4.29-4.75 (4H,m), 2.91-3.33 (4H,q), 1.31 (8H,bs).

9.4 1,8-divinyloctyldicarbamate

To a 500 mL 3-neck round bottom flask fitted with a magnetic stirrer, condenser, nitrogen blanket, dropping funnel, thermometer was added 5.0 g (34.6 mmol) of 1,8 diaminooctane, 6.1 g (76.1 mmol) of pyridine, 100 mL anhydrous acetonitrile, 100 mL ether. After the starting material was dissolved 8.0 g (87 mmol) of vinyl chloroformate was added over 20 minutes an exotherm was noted, and a precipitate formed over 18 hours. The solvent was removed on a rotary evaporator and the residue was dissolved in methylene chloride, washed with 2N NaOH, thrice with distilled water then dried with magnesium sulfate. The solid was coated on silica gel and chromatographed (97% CH₂Cl₂, 3% ETOAc) to give a solid that was dissolved in methylene chloride and slowly added to stirred heptane. The solid recovered was dried to give 6.7 g (22.1 mmol, 64.1% yield) melting point 83°-88° C. FTIR 3336.20, 3086.75, 3032.18, 2996.55, 2942.19, 2926.73, 2872.60, 2855.14, 1709.82, 1676.68, 1649.06, 1530.29, 1478.71, 1464.03, 1362.59, 1308.80, 1257.38, 1252.87, 1213.85, 1168.05, 1083.04, 1062.73, 1031.76, 956.24, 874.73, 861.46. NMR (CDCl₃) 6.95-7.34 (2H,q), 4.62-5.13 (2H,bs), 4.29-4.75 (4H,m), 2.97-3.30 (4H,q), 1.31 (10H,bs).

PART X—FLUOROALKYL BRIDGED CROSSLINKERS

10.0

1,5-bis-(Vinyloxycarbonyloxy)-2,2,3,3,4,4-hexafluoropentane $C_{11}H_{10}F_6O_6$ To a 500 mL 3-neck round bottom flask fitted with a magnetic stirrer, condenser, nitrogen blanket, thermometer, dropping funnel, and ice-water bath was added 12.3 g (155.5 mmol) of pyridine and 200 mL of methylene chloride. After cooling to 5° C.±2° C. add 16.57 g (155.5mmol) of vinyl chloroformate was added so that the temperature was maintained. A white precipitate formed immediately. When the addition was complete, 15.0 g (70.7 mmol) of 2,2,3,3,4,4-hexafluoro-1,5-pentanediol in one portion as a slurry with 250 mL methylene chloride was added. The reaction was allowed to warm to room temperature for 18 hours. The organics were washed twice with 250 mL of 2N HCl then dried with magnesium sulfate. The solvent was removed on a rotary evaporator to afford 24.7 g of a straw oil. Following chromatography (silica gel, toluene), 21.8 g (61.9 mmol, 87.6%) of colorless oil was obtained. FTIR (neat, capillary) 3102.29, 2983.43, 1767.41, 1651.43, 1442.83, 1404.75, 1303.52, 1247.26, 1151.88, 1125.91, 1095.64, 1031.24, 1005.65, 985.71, 939.37, 882.43, 776.53, 697.20, 673.23, 650.18. NMR (CDCl₃)δ 6.83-7.26 (2H,m), 4.30-5.23 (8H,m).

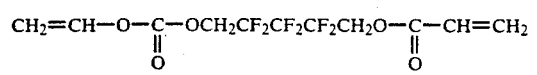

COPOLYMER FILM EXAMPLES

A. Hydrogel Materials

Soft hydrogel copolymers of the present invention were produced by copolymerizing a monomer of the formula

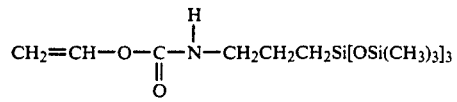

with N-vinylpyrrolidinone (NVP), and the crosslinker monomer 1,5-bis-(vinyloxycarbonyloxy)-2,2,3,3,4,4-hexacluoropentane, in the presence of a nonreactive diluent and a UV irradiation, free radical initiator in the following weight ratios:

| film # | hydrophilic monomer | NVP | X-linkers | % H₂O | DK × 10⁻¹¹ |
|---|---|---|---|---|---|
| 1 | 22.5 | 65.0 | 2.5 | 73 | 45 |
| 2 | 62.5 | 25.0 | 2.5 | 19 | 91 |
| 3 | 64.5 | 24.7 | 0.5 | 25 | 97 |
| 4 | 23.5 | 45.0 | 1.5 | 63 | 41 |
| 5 | 53.5 | 25.0 | 1.5 | 27 | 79 |
| 6 | 42.5 | 25.0 | 2.5 | 33 | 65 |
| 7 | 2.5 | 65.0 | 2.5 | 85 | 56 |
| 8 | 23.5 | 65.0 | 1.5 | 77 | 51 |
| 9 | 44.5 | 45.0 | 0.5 | 58 | 46 |
| 10 | 21.5 | 64.7 | 0.9 | 80 | 49 |
| 11 | 43.1 | 43.1 | 0.9 | 53 | 47 |
| 12 | 64.7 | 21.5 | 0.9 | 23 | 115 |
| 13 | 32.5 | 45.0 | 2.5 | 51 | 37 |

These films were prepared by placing the prepolymer mixtures between glass plates separated by a Teflon ® peripheral gasket and were UV irradiated for 2 hours. The samples were then prepared for physical characterization.

Physical properties for films were determined using the following test procedures:

1. Tensile strength (g/mm²) and modulus of elasticity were measured per ASTM test a method D1708.
2. Elongation was measured per ASTM 1708.
3. Initial tear strength and propagation tear strength were measured per ASTM 1438.
4. Oxygen permeabilities were measured by the method reported by Relojo, M. et al in *Contact and Intraocular Lens Medical Journal*, Vol. 3, issued p. 27 (1977) and edge effects were accounted for per the methods described by Fatt, et al. in *International Contact Lens Clinic*, v. 14, p. 389 (1987).
5. Water content is measured per a gravimetric method.
6. Refractive index was measured per typical methods on hydrated samples using a refractometer.

The physical characterization of these films is reported in the following table.

| Film | Modulus (g/mm²) | Tensile (g/mm²) | Elongation % | Tear (initial/propagation) (g/mm²) |
|---|---|---|---|---|
| 1 | 38 | 15 | 60 | 1.4/1.0 |
| 2 | 970 | 170 | 130 | 52/52 |
| 3 | 203 | 77 | 330 | 56/56 |
| 4 | 52 | 28 | 70 | 1.4/1.4 |
| 5 | 370 | 100 | 160 | 30/30 |
| 6 | 262 | 72 | 90 | 17/17 |
| 7 | 27 | 7 | 42 | —/— |

-continued

| Film | Modulus (g/mm$^2$) | Tensile (g/mm$^2$) | Elongation % | Tear (initial/ propagation) (g/mm$^2$) |
|---|---|---|---|---|
| 8 | 17 | 13 | 120 | 1.1/1.0 |
| 9 | 18 | 20 | 280 | 6.5/6.5 |
| 10 | 72 | 43 | 75 | 0.8/0.6 |
| 11 | 49 | 27 | 180 | —/5.5 |
| 12 | 430 | 110 | 200 | —/46 |
| 13 | 86 | 40 | 70 | 3.2/3.1 |

As can be seen, all of the above film samples meet the general requirements for a hydrogel contact lens material.

B. Hard Contact Lens Material Examples

Hard, gas permeable contact lens materials were made using the novel vinylcarbonate functional monomers described herein by polymerizing 1,1,1,3,3,3-hexafluoroprop-2-yl vinyl carbonate (hfpvc)

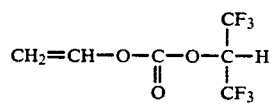

with a variety of hydrophilic monomers and crosslinkers, such as those known in the prior art and the preferred hydrophilic monomers and crosslinkers disclosed herein.

Other materials can be made by substituting the 1,1,1,3,3,3-hexafluoroprop-2-yl vinyl carbonate monomer with a fluoroalkyvinyl carbonate or carbamate monomer preferably chosen from the group consisting of trifluoroethyl vinyl carbonate (tfevc); 1,5-bis-(Vinyloxycarbonyloxy)-2,2,3,3,4,4-hexafluoropentane (hfpdvc); and 2,2,2-trifluoro-1-phenylethyl Vinyl carbonate (tfpvc).

Films were made by the general method described in the hydrogel film example. The films were polymerized from monomer mixtures with the following formulations.

| film #14: | 65 wt % hfpvc |
| | 30 wt % 3-[tris(trimethylsiloxy)silyl]propyl vinyl carbamate |
| | 5 wt % hfpdvc and about |
| | 0.5 wt % free radical initiator |
| film #15: | 65 wt % hfpvc |
| | 30 wt % 3[tris(trimethylsiloxy)silyl]propyl vinyl carbonate and |
| | 0.5 wt % free radical initiator |
| film #16: | 65 wt % hfpvc |
| | 30 wt % 3-[tris(trimethylsiloxy)silyl] propyl vinyl carbamate |
| | 4.0 wt % 2,2-dimethyl-1,3-bis(vinyloxycarbonyloxy)propane |
| | 0.5 wt % free radical initiator |
| film #17: | 60 wt % hfpvc |
| | 25 wt % 3[tris(trimethylsiloxy)silyl] propyl vinyl carbonate |
| | 5 wt % V$_2$D$_{25}$ |
| | 5 wt % 2,2-dimethyl-1,3-bis(vinyloxycarbonyloxy)propane |
| | 5 wt % N-vinyl-2-pyrrolidinone |
| | 0.5 wt % free radical initiator |
| film #18: | 60 wt % hfpvc |
| | 25 wt % 3[tris(trimethylsiloxy)silyl]propyl vinyl carbonate |
| | 5 wt % V$_2$D$_{25}$ |
| | 5 wt % hfpdvc |
| | 5 wt % N-vinyl-2-pyrrolidinone |
| | 0.5 wt % free radical initiator |
| film #19: | 60 wt % hfpvc |
| | 25 wt % 3-(vinyloxycarbonylthio)propyl-[tris(trimethylsiloxy)silane] |
| | 5 wt % V$_2$D$_{25}$ |
| | 5 wt % hfpdvc |
| | 5 wt % N-vinyl-2-pyrrolidinone |
| | 0.5 wt % free radical initiator |
| film #20: | 60 wt % hfpvc |
| | 25 wt % 3-tris(trimethylsiloxy) propylsilane allylcarbamate |
| | 5 wt % V$_2$D$_{25}$ |
| | 5 wt % 2,2,3,3,4,4-hexafluoro-1,5-pentane dinvinylcarbonate |
| | 5 wt % N-vinyl-2-pyrrolidinone |
| | 0.5 wt % free radical initiator |

The physical characteristics of these films as measured are reported in the following table.

| film # | modulus (g/mm$^2$) | tensile (g/mm$^2$) | % elongation | O2 Perm × 10$^{-11}$ |
|---|---|---|---|---|
| 14 | 75000 | 1250 | 14 | 130 |
| 15 | 82000 | 1500 | 13 | 140 |
| 16 | 80000 | 2100 | 8 | 130 |
| 17 | 73000 | 2000 | 8 | 120 |
| 18 | 85000 | 1600 | 16 | 130 |
| 19 | 84000 | 1800 | 7 | 100 |
| 20 | 101000 | 2500 | 7 | 100 |

All of these films are acceptable as hard gas permeable contact lens materials.

c. Soft Non-Hydrogel Material Examples

A series of films were made by the general film casting technique described in the hydrogel materials example except that prepolymer mixtures for the various films were employed as hereinafter disclosed.

| film #21: | 50 wt % 3-(trimethylsilyl)propyl vinyl carbonate |
| | 35 wt % 3-[tris(trimethylsiloxy)silyl]propyl vinyl carbamate |
| | 10 wt % N-vinyl-2-pyrrolidinone |
| | 5 wt % 2,2-dimethyl-1,3-bis(vinyloxycarbonyloxy)propane |
| | 0.5 wt % UV free radical initiator |
| film #22: | 25 wt % 3-(trimethylsilyl)propyl vinyl carbonate |
| | 64 wt % 3-[tris(trimethylsiloxy)silyl]propyl vinyl carbamate |
| | 10 wt % N-vinyl-2-pyrrolidinone |
| | 1 wt % 2,2-dimethyl-1,3-bis(vinyloxycarbonyloxy)propane |
| | 0.5 wt % UV free radical initiator |
| film #23: | 44 wt % 3-(trimethylsilyl)propyl vinyl carbonate |
| | 44 wt % 3-[tris(trimethylsiloxy)silyl]propyl vinyl carbamate |
| | 10.5 wt % N-vinyl-2-pyrrolidinone |
| | 1 wt % 2,2-dimethyl-1,3-bis(vinyloxycarbonyloxy)propane |
| | 0.5 wt % UV free radical initiator |
| film #24: | 54 wt % 3-(trimethylsilyl)propyl vinyl carbonate |
| | 35 wt % 3-[tris(trimethylsiloxy)silyl]propyl vinyl carbamate |
| | 10 wt % N-vinyl-2-pyrrolidinone |
| | 1 wt % 2,2-dimethyl-1,3-bis(vinyloxycarbonyloxy)propane |
| | 0.5 wt % UV free radical initiator |
| film #25: | 65 wt % 3-(trimethylsilyl)propyl vinyl carbonate |
| | 25 wt % 3-[tris(trimethylsiloxy)silyl]propyl vinyl carbamate |
| | 10 wt % N-vinyl-2-pyrrolidinone |
| | 1 wt % 2,2-dimethyl-1,3-bis(vinyloxycarbonyloxy)propane |
| | 0.5 wt % UV free radical initiator |
| film #26: | 40 wt % 3-(trimethylsilyl)propyl vinyl carbonate |
| | 40 wt % 3-[tris(trimethylsiloxy)silyl]propyl |

| | |
|---|---|
| | vinyl carbamate |
| | 20 wt % N-vinyl-2-pyrrolidinone |
| | 1 wt % 2,2-dimethyl-1,3-bis(vinyloxy-carbonyloxy)propane |
| | 0.5 wt % UV free radical initiator |
| film #27: | 34 wt % 3-(trimethylsilyl)propyl vinyl carbonate |
| | 34 wt % 3-[tris(trimethylsiloxy)silyl]propyl vinyl carbamate |
| | 30 wt % N-vinyl-2-pyrrolidinone |
| | 1 wt % 2,2-dimethyl-1,3-bis(vinyloxy-carbonyloxy)propane |
| | 0.5 wt % UV free radical initiator |
| film #28: | 28 wt % 3-(trimethylsilyl)propyl vinyl carbonate |
| | 68 wt % 3-[tris(trimethylsiloxy)silyl]propyl vinyl carbamate |
| | 4 wt % N-vinyl-2-pyrrolidinone |
| | 1 wt % 2,2-dimethyl-1,3-(vinyloxy-carbonyloxy)propane |
| | 0.5 wt % UV free radical initiator |
| film #29: | 20 wt % trimethylsilylmethyl vinyl carbonate |
| | 70 wt % 3-[tris(trimethylsiloxy)silyl]propyl vinyl carbamate |
| | 10 wt % N-vinyl-2-pyrrolidinone |
| | 1 wt % 2,2-dimethyl-1,3-(vinyloxy-carbonyloxy)propane |
| | 0.5 wt % free radical initiator |
| film #30: | 20 wt % trimethylsilylethyl vinyl carbonate |
| | 70 wt % 3-[tris(trimethylsiloxy)silyl]propyl vinyl carbamate |
| | 10 wt % N-vinyl-2-pyrrolidinone |
| | 1 wt % 2,2-dimethyl-1,3-bis(vinyloxy-carbonyloxy)propane |
| | 0.5 wt % free radical initiator |

The films were cured, samples were taken of the film and the following characteristics measured:

| film # | modulus (g/mm$^2$) | tensile strength (g/mm$^2$) | % elongation | Tear Strength (initial/propagation) | O$_2$ DK × 10$^{-11}$ |
|---|---|---|---|---|---|
| 21 | 2200 | 440 | 106 | 120/120 | 76 |
| 22 | 270 | 150 | 234 | 80/80 | 140 |
| 23 | 143 | 140 | 266 | 70/70 | 100 |
| 24 | 120 | 140 | 270 | 70/70 | 90 |
| 25 | 110 | 120 | 270 | 80/80 | 72 |
| 26 | 35 | 40 | 210 | 14/14 | 56 |
| 27 | 50 | 70 | 290 | 30/30 | 80 |
| 28 | 400 | 120 | 200 | 100/100 | 110 |
| 29 | — | — | — | — | 100 |
| 30 | — | — | — | — | 100 |

The above sample films demonstrated characteristics which would be useful as a soft, elastomeric, contact lens material with low or no water content.

1,2,3-tris(vinyloxycarbonyloxy)propane

To a 250 ml three neck round bottom flask fitted with a mechanical stirrer, condensor, nitrogen blanket, and a dropping funnel was added 3.1 g (33.7 mmol) of glycerol, 8.7 g (110 mmol) of pyridine and 125 mL of anhydrous acetonitrile. The reaction flask was cooled in an ice water bath so that the temperature did not exceed 5° C. To the reaction mixture was added 11.7 g (110 mmol) of vinylchloro formate over 30 minutes. The reaction mixture was allowed to stir to room temperature overnight. The solvent was removed on a rotary evaporator and the crude product was taken up in ethyl acetate and washed with 2 100 mL portions of 2N HCl, then 2 100 mL portions of 2N NaOH, then 2 100 mL portions of brine. The organics were dried with magnesium sulfate, the the solvent removed and the crude product is distilled to obtain the pure product.

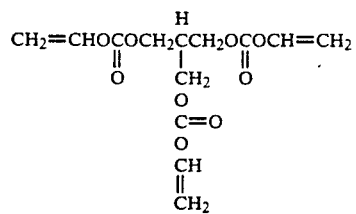

1,3-bis(vinyloxycarbonyloxy)-2,2- bis(vinyloxycarbonyloxymethyl) propane

To a 250 ml three neck round bottom flask fitted with a mechanical stirrer, condensor, nitrogen blanket, and a dropping funnel was added 3.0 g (22.0 mmol) of pentaerythritol, 7.7 g (97 mmol) of pyridine and 125 mL of anhydrous acetonitrile. The reaction flask was cooled in an ice water bath so that the temperature did not exceed 5° C. To the reaction mixture was added 10.3 g (97 mmol) of vinylchloroformate over 30 minutes. The reaction mixture was allowed to stir at room temperature overnight. The solvent was removed on a rotary evaporator and the crude product was taken up in ethyl acetate and washed with two 100 mL portions of 2N HCl, then two 100 mL portions of 2N NaOH, then two 100 mL portions of brine. The organic phase was dried with magnesium sulfate, the the solvent removed and the crude product distilled to obtain the pure product.

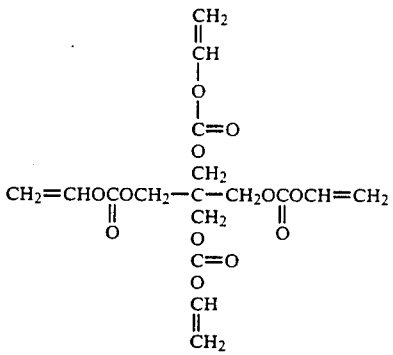

V$_2$DF$_{25}$

To a 100 mL one neck round bottom flask fitted with a magnetic stirrer, and a drying tube was added 5.0 g (11.95 mmol) of 1,3-bis (4-vinylbutylcarbonate) tetramethyldisiloxane, and 46.6 g (99.6 mmol) of 1,3,5-methyl,1,3,5-trifluoropropylcyclotrisiloxane. To the reaction mixture was added 0.0679 g (0.452 mmol) of triflurormethanesulfonic acid. The mixture was stirred at room temperature for 24 hours then 0.38 g (4.52 mmol) of sodium bicarbonate was added, and the mixture was allowed to stir an addtional 24 hours. The reaction mixture was filtered thruogh 20.0 g of activated F20 alumina to give a lite yellow oil. The crude product was vacuum stripped at 90° C. 0.025 Torr for 4 hours to give the desired product.

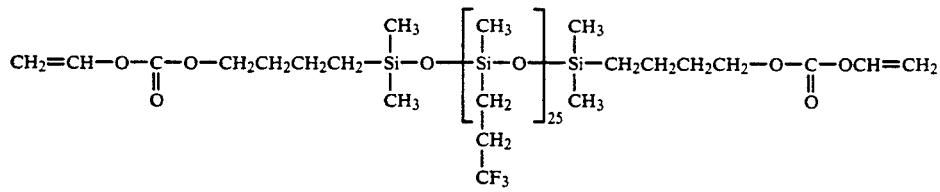

What is claimed is:

1. Compounds of the general formula

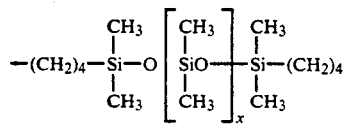

wherein
$R^2$ denotes —H or —$CH_3$;
b is 0 or 1;
a is 1, 2, 3, or 4; and
R is an organosilicon radical chosen from the groups of radicals represented by the formulae:

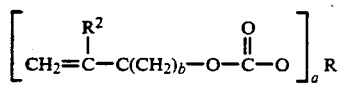

wherein x is 25 on the average;

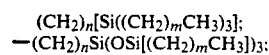

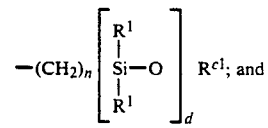

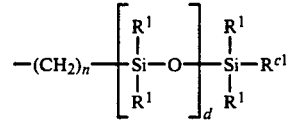

where $R^1$ denotes a monovalent organic radical selected from the group consisting of an alkyl radical with 1 to 6 carbon atoms, or a fluoroalkyl radical with 1 to 6 carbon atoms;
$R^{cl}$ denotes

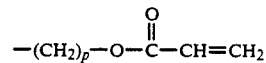

p is 1 to 6; m is 0 to 5; and
d is 1-200.

2. The compound of claim 1, trimethylsilylmethyl vinyl carbonate.

3. The compound of claim 1, trimethylsilylethyl vinyl carbonate.

4. The compound of claim 1, 3-(trimethylsilyl)propyl vinyl carbonate.

5. The compound of claim 1, t-butyldimethylsiloxyethyl vinyl carbonate.

6. The compound of claim 1, 3-[tris(trimethylsiloxy) silyl]propyl vinyl carbonate.

7. The compound of claim 1, 1,3-bis[4-(vinyloxycarbonyloxy)but-1-yl]-tetramethyl disiloxane.

8. The compound 3-[tris(trimethylsiloxy) silyl]-propylaminoethyl vinyl carbonate.

* * * * *

UNITED STATES PATENT AND TRADEMARK OFFICE
CERTIFICATE OF CORRECTION

PATENT NO. : 5,070,215
DATED : December 3, 1991
INVENTOR(S) : Donald E. Bambury and David E. Seelye It is certified that error appears in the above-identified patent and that said Letters Patent is hereby corrected as shown below:

Column 2, line 59, insert --should be-- after "angle".

Column 9, line 19, change "8.779" to --8.77--.

Column 10, line 33, change "707 81." to --707.81.--.

Column 12, lines 25-29, delete the structural diagram and insert the following:

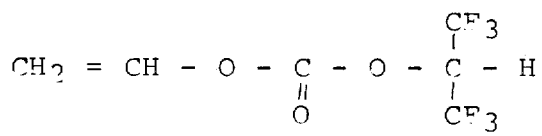

Column 15, line 33, change "91H,m)" to --(1H,m)--.

Column 17, lines 53-58, delete the structural diagram and insert the following:

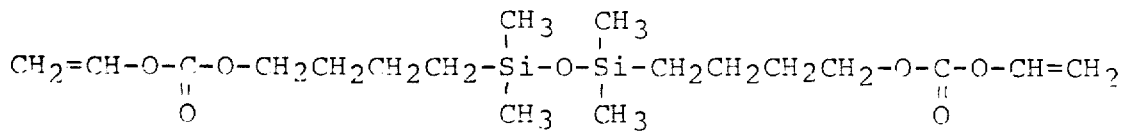

Column 18, line 20, change "Tris(trimethylsiloxy)silylpropyl" to --[Tris(trimethylsiloxy)silylpropyl]--.

Column 19, lines 36-40, delete the structural formula and insert the following:

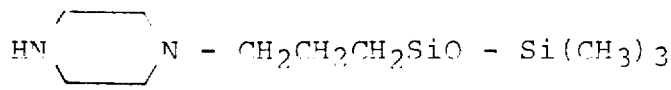

UNITED STATES PATENT AND TRADEMARK OFFICE
CERTIFICATE OF CORRECTION

PATENT NO. : 5,070,215
DATED : December 3, 1991
INVENTOR(S) : Donald E. Bambury and David E. Seelye It is certified that error appears in the above-identified patent and that said Letters Patent is hereby corrected as shown below:

Column 29, line 49, change "N,O-bis-(Vinyloxycarbonyl)ethanolamine $C_8H_{11}O_5$" to --N,O-bis-(Vinyloxycarbonyl)ethanolamine $C_8H_{11}O_5$--.

Column 36, at the beginning of line 1, delete "the".

Claim 8, line 1, insert --of claim 1, -- after the word "compound".

Signed and Sealed this

Twenty-first Day of December, 1993

Attest:

BRUCE LEHMAN

Attesting Officer  Commissioner of Patents and Trademarks

UNITED STATES PATENT AND TRADEMARK OFFICE
CERTIFICATE OF CORRECTION

PATENT NO. : 5,070,215
DATED : December 3, 1991
INVENTOR(S) : Ronald E. Bambury and David E. Seelye It is certified that error appears in the above-identified patent and that said Letters Patent is hereby corrected as shown below:

Column 36, line 5, delete the structural formula and insert the following:

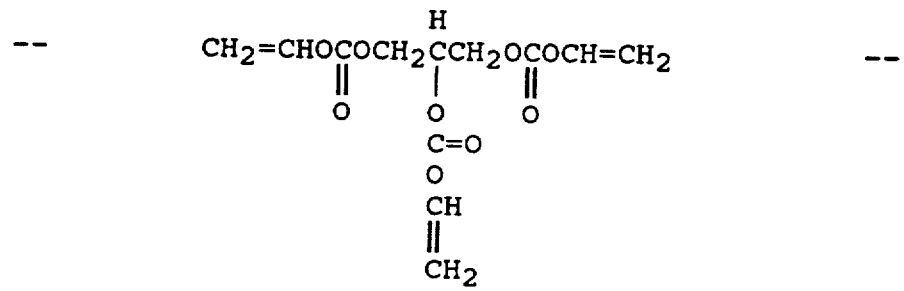

Claim 1, line 2, delete the structural formula and insert the following:

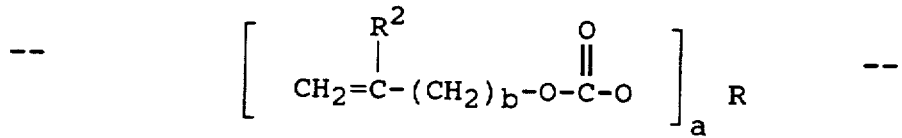

Claim 1, line 9, in the structural formula, replace the right terminal group "$(CH_2)_4$" with   -- $(CH_2)_4$—  --.

Claim 1, line 11, delete the structural formula and insert the following:

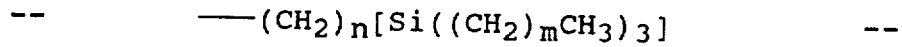

UNITED STATES PATENT AND TRADEMARK OFFICE
CERTIFICATE OF CORRECTION

PATENT NO. : 5,070,215

DATED : December 3, 1991

INVENTOR(S) : Ronald E. Bambury and David E. Seelye

It is certified that error appears in the above-identified patent and that said Letters Patent is hereby corrected as shown below:

Column 19, line 10, delete the structural formula and insert the following:

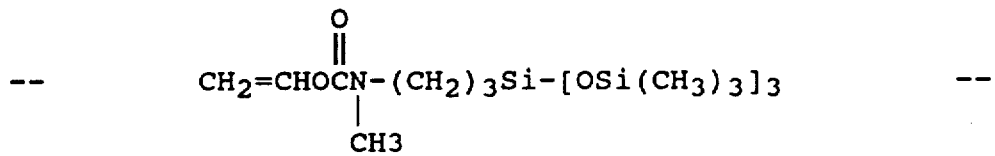

Column 27, line 5, delete the structural formula and insert the following:

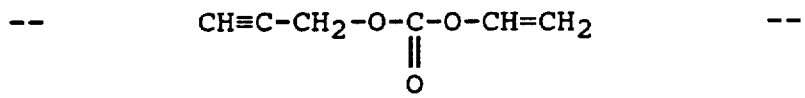

Column 31, last line, delete the structural formula and insert the following:

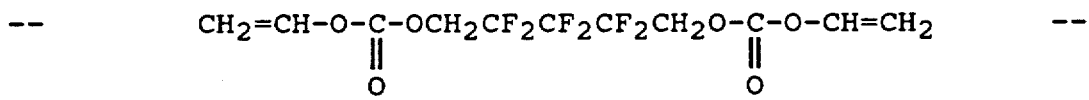

Column 32, line 15, correct the spelling of
-- hexafluoropentane --.

UNITED STATES PATENT AND TRADEMARK OFFICE
CERTIFICATE OF CORRECTION

PATENT NO. : 5,070,215

DATED : December 3, 1991

INVENTOR(S) : Ronald E. Bambury and David E. Seelye

It is certified that error appears in the above-identified patent and that said Letters Patent is hereby corrected as shown below:

Claim 1, line 12, delete the structural formula and insert the following:

-- $—(CH_2)_n Si(OSi[(CH_2)_m CH_3]_3)_3$ --

Claim 1, penultimate line after "m is 0 to 5;", insert -- n is 1 to 4; --.

Signed and Sealed this

Nineteenth Day of July, 1994

BRUCE LEHMAN

Attest:

Attesting Officer

Commissioner of Patents and Trademarks